(12) United States Patent
Kano

(10) Patent No.: US 10,835,308 B2
(45) Date of Patent: Nov. 17, 2020

(54) TUBE, TUBE UNIT, AND SUCTION/FLUID SUPPLY UNIT

(71) Applicant: OLYMPUS CORPORATION, Hachioji (JP)

(72) Inventor: Akihito Kano, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 175 days.

(21) Appl. No.: 16/198,092

(22) Filed: Nov. 21, 2018

(65) Prior Publication Data

US 2019/0090938 A1 Mar. 28, 2019

Related U.S. Application Data

(63) Continuation of application No. PCT/JP2016/065489, filed on May 25, 2016.

(51) Int. Cl.
*A61B 18/14* (2006.01)
*A61B 17/32* (2006.01)
(Continued)

(52) U.S. Cl.
CPC .. *A61B 18/1445* (2013.01); *A61B 17/320092* (2013.01); *A61B 18/085* (2013.01);
(Continued)

(58) Field of Classification Search
CPC .......... A61B 17/320092; A61B 18/085; A61B 18/1445; A61B 2017/32007; A61B 2017/32008; A61B 2017/320084; A61B 2017/320094; A61B 2018/00404; A61B 2018/0063; A61B 2018/00982; A61B 2018/142; A61B 2218/002; A61B 2218/007; A61B 17/32; A61B 17/320068; A61B 18/00; A61B 18/04; A61B 18/08; A61B 18/082; A61B 18/12;
(Continued)

(56) References Cited

U.S. PATENT DOCUMENTS

2006/0265035 A1* 11/2006 Yachi ............... A61B 17/32009
607/101
2014/0142572 A1* 5/2014 Maehara ............ A61B 18/1445
606/46

(Continued)

FOREIGN PATENT DOCUMENTS

JP 2000-502585 A 3/2000
JP 2001-445 A 1/2001
(Continued)

OTHER PUBLICATIONS

Oct. 8, 2019 Office Action issued in Japanese Patent application No. 2018-518872.

(Continued)

*Primary Examiner* — Jason E Flick
(74) *Attorney, Agent, or Firm* — Oliff PLC

(57) ABSTRACT

A tube configured to be mounted on an outer side of a shaft of a treatment instrument includes a tube main body, and a convex portion that is provided along a longitudinal axis of the tube main body and is protruded inwards in a radial direction of the tube main body with respect to an inner peripheral surface of the tube main body.

14 Claims, 16 Drawing Sheets

(51) Int. Cl.
    *A61B 18/08* (2006.01)
    *A61B 18/00* (2006.01)

(52) U.S. Cl.
    CPC ............. *A61B 2017/32007* (2017.08); *A61B 2017/32008* (2013.01); *A61B 2017/320084* (2013.01); *A61B 2017/320094* (2017.08); *A61B 2018/0063* (2013.01); *A61B 2018/00404* (2013.01); *A61B 2018/00982* (2013.01); *A61B 2018/142* (2013.01); *A61B 2218/002* (2013.01); *A61B 2218/007* (2013.01)

(58) Field of Classification Search
    CPC .... A61B 18/1442; A61B 2017/320072; A61B 2017/320092; A61B 2018/00315; A61B 2018/00345; A61B 2018/00571; A61B 2018/1405
    See application file for complete search history.

(56) References Cited

U.S. PATENT DOCUMENTS

2016/0000459 A1\* 1/2016 Palmerton ............. A61B 90/30
                                                    604/541
2017/0105790 A1   4/2017 Onuma

FOREIGN PATENT DOCUMENTS

| JP | 2006-341066 A | 12/2006 |
| JP | 2009-233269 A | 10/2009 |
| JP | 2014-100369 A | 6/2014 |
| JP | 2016-49364 A | 4/2016 |
| WO | 2016/006379 A1 | 1/2016 |
| WO | 2016/009702 A1 | 1/2016 |

OTHER PUBLICATIONS

Aug. 23, 2016 International Search Report issued in International Patent Application PCT/JP2016/065489.
Nov. 27, 2018 International Preliminary Report on Patentability issued in International Patent Application PCT/JP2016/065489.

\* cited by examiner

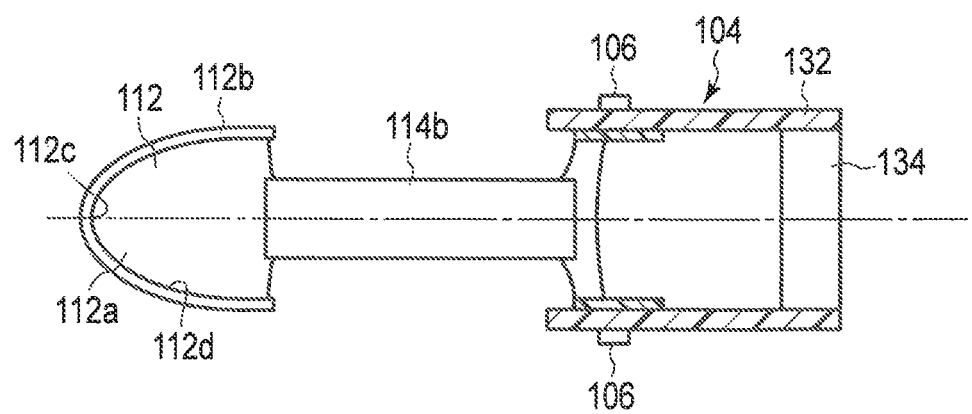
F I G. 11B
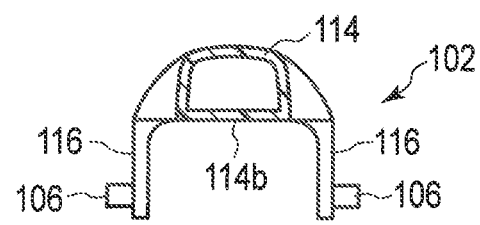
F I G. 11C
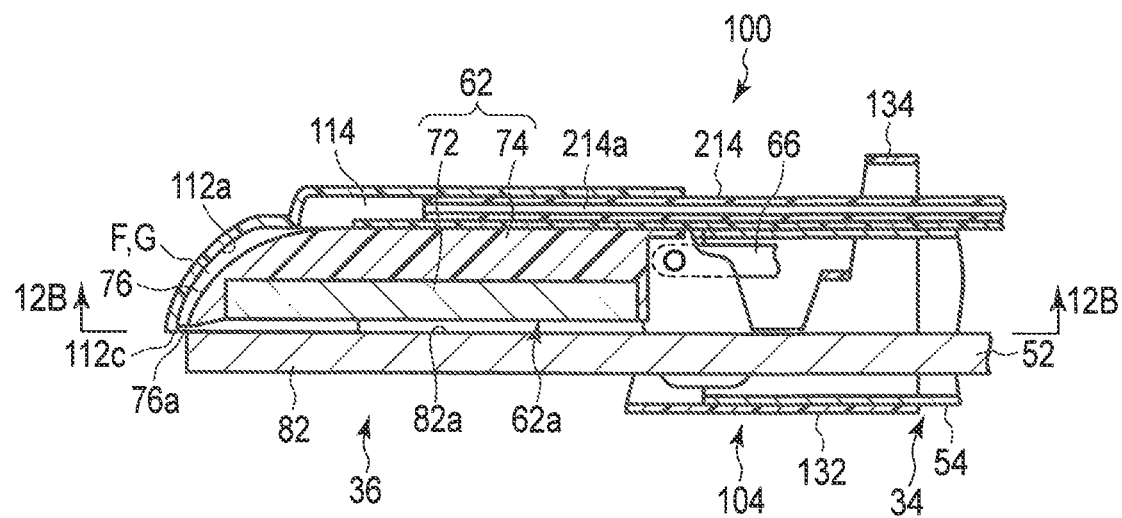
F I G. 12A

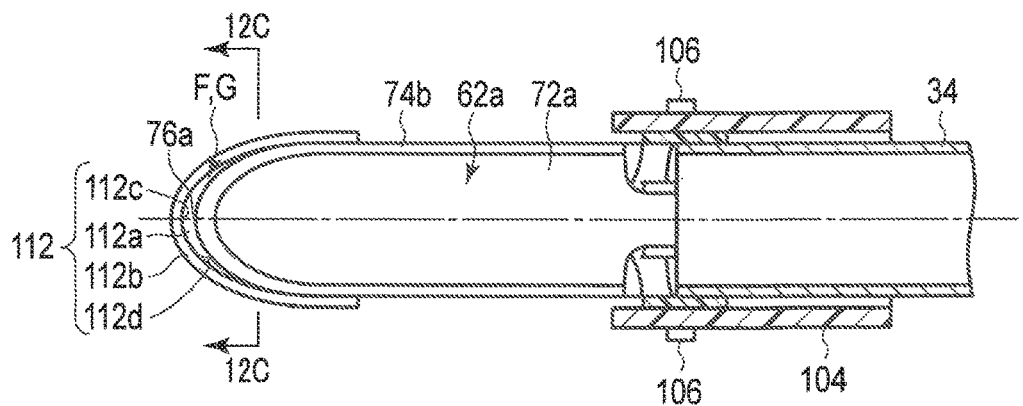
F I G. 12B
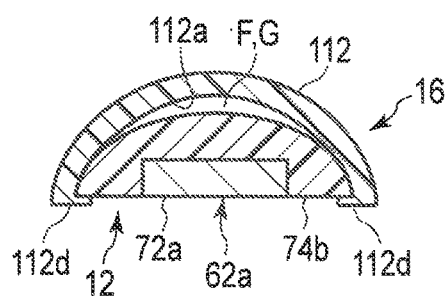
F I G. 12C
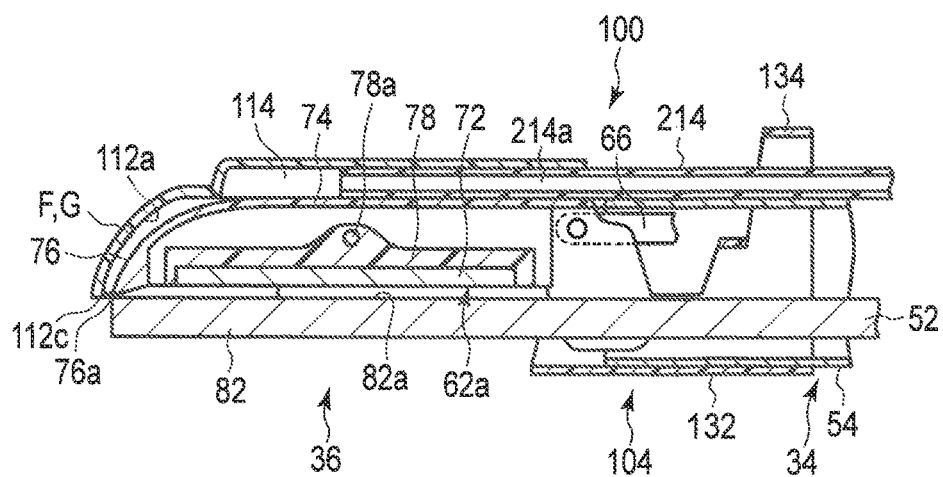
F I G. 13

TUBE, TUBE UNIT, AND SUCTION/FLUID SUPPLY UNIT

CROSS-REFERENCE TO RELATED APPLICATIONS

This application is a Continuation Application of PCT Application No. PCT/JP2016/065489, filed May 25, 2016, the entire contents of which are incorporated herein by reference.

BACKGROUND OF THE INVENTION

1. Field of the Invention

The present invention relates generally to a tube and a tube unit that are used by being mounted on at outer side of a shaft of a treatment instrument, in addition to a suction/fluid supply unit having the tube.

2. Description of the Related Art

A treatment instrument including a suction channel is disclosed, for example, in Jpn. Pat. Appln. KOKAI Publication NO. 2001-445.

When performing suction in a state where a treatment portion of the treatment instrument is arranged within a body cavity, clogging may occur in the suction channel. In this case, to solve clogging of the suction channel, the treatment portion of the treatment instrument is temporarily taken outside the body, etc. to secure the suction channel.

BRIEF SUMMARY OF THE INVENTION

According to one aspect of the present invention, a tube configured to be mounted and used on an outer side of a shaft of a treatment instrument, includes: a tube main body, a first convex portion, a first lumen, and a pipe line. The tube main body extends along a longitudinal axis defined by a distal end and a proximal end, and includes an inner circumferential surface. The first convex portion is provided along the longitudinal axis, and includes a first convex surface which is protruded inward in a radial direction of the tube main body with respect to the inner circumferential surface of the tube main body, and which is configured to come into contact with an outer circumferential surface of the shaft. The pipe line extends in the first convex portion along the longitudinal axis, and is configured to pass a fluid. The first convex portion and the inner circumferential surface of the tube main body form a first lumen in cooperation with the outer circumferential surface of the shaft. The first lumen is located at a position adjacent to the first convex portion in a circumferential direction of the longitudinal axis.

Advantages of the invention will be set forth in the description which follows, and in, part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 11B is a schematic partial cross-sectional view showing a state in which the fluid supply instrument of the fluid suction/fluid supply unit of the treatment system according to the second embodiment is viewed from a position taken along line 11B-11B in FIG. 11A.

FIG. 11C is a cross-sectional view of the fluid supply instrument of the fluid suction/fluid supply unit of the treatment system according to the second embodiment taken along line 11C-11C in FIG. 11A.

FIG. 12A is a schematic cross-sectional view showing a state in which a treatment instrument unit is configured by mounting the fluid supply instrument of the fluid suction/fluid supply unit on the first grasping section of the end effector of the treatment instrument of the treatment system according to the second embodiment.

FIG. 12B is a schematic view showing a state in which the treatment instrument unit configured by Mounting the fluid supply instrument of the fluid suction/fluid supply unit on the first grasping section of the end effector of the treatment instrument of the treatment system according to the second embodiment is viewed from a position taken along line 12B-12E in FIG. 12A.

FIG. 12C is a schematic view showing a state in which the fluid supply instrument of the fluid suction/fluid supply unit mounted on the first grasping section of the end effector of the treatment instrument of the treatment system according to the second embodiment is viewed from a position taken along line 12C-12C in FIG. 12A and FIG. 12B.

FIG. 13 is a schematic cross-sectional view showing a state in which a treatment instrument unit is configured by mounting a fluid supply instrument of a fluid suction/fluid supply unit on the first grasping section of the end effector of the treatment instrument of a treatment system according to the third embodiment.

DETAILED DESCRIPTION OF THE INVENTION

Hereinafter, embodiments for implementing the present invention will be explained with reference to the drawings.

First Embodiment

A first embodiment will be explained with reference to FIG. 1 to FIG. 9.

Figure 1:
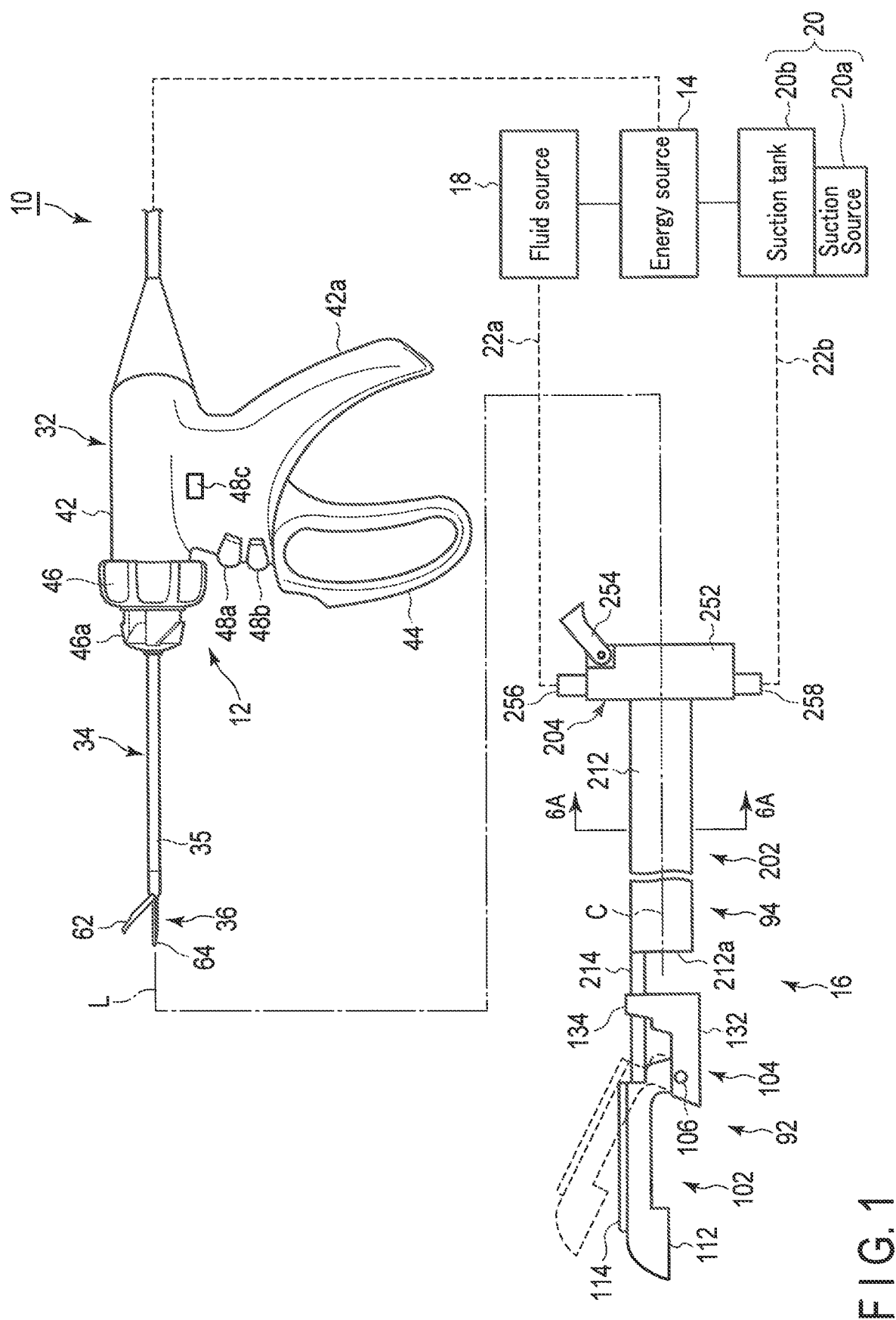
FIG. 1 is a schematic view showing a treatment system according to first to sixth embodiments.

As shown in FIG. 1, a treatment system 10 according to the present embodiment includes a treatment instrument (surgical operation device) 12, an energy source (controller) 14 configured to output appropriate power and/or signals in accordance with operations of switches 48a, 48b, and 48c explained later on, a fluid suction/fluid supply unit (fluid suction/fluid supply aid equipment) 16, a fluid source 18, and a fluid suction apparatus 20. The fluid suction apparatus 20 includes a suction source (suction pump) 20a and a suction tank 20b. The treatment instrument 12 is connected to the energy source 14 and is used as an energy treatment instrument.

The fluid suction/fluid supply unit 16 is attached to the treatment instrument 12 and used. A state in which the fluid suction/fluid supply unit 16 is attached to the treatment instrument 12 is defined as a treatment instrument unit 100. The fluid suction/fluid supply unit 16 is used by being connected to the fluid source 18 and the fluid suction apparatus 20. Here, an example of using the fluid source 18 as a liquid supplying source is explained; however, this may also be used as an air supply source.

Furthermore, an input unit (not shown), etc. for performing various settings is connected to the energy source 14.

In this embodiment, the treatment instrument 12 includes a handle 32, a shaft 34, and an end effector 36. The handle 32, the shaft 34, and the end effector 36 define a longitudinal axis L of the treatment instrument 12. Since the longitudinal axis L is defined along the shaft 34 and/or the end effector 36, it may be straight or curved.

The shaft 34 is supported by the handle 32 and protrudes on a distal end side of the handle 32 along the longitudinal axis L. The end effector 36 is disposed on a distal end side with respect to a distal end of the shaft 34 along the longitudinal axis L.

Various shapes of the handle 32 are permitted. Here, a case where the handle 32 is a pistol type (gun type) will be explained as an example. The handle 32 includes a housing 42 including a fixed handle (grip) 42a, and a movable handle 44 provided on the housing 42 and movable between positions spaced apart from and adjacent to the fixed handle 42a. The handle 32 includes a rotation knob 45 on a distal end portion of the housing 42 configured to rotate the shaft 34 and the end effector 36 about the longitudinal axis L of the handle 32. Since the relationship between the rotation knob 46 and the shaft 34 and the end effector 36 are well-known, the explanation will be omitted here. The rotation knob 46 includes a concave fixing portion (concave portion) 46a which receives a fixing arm 254 of a connection portion 204 of a tube unit (fluid (liquid) supply path) 94 explained later on. When the fixing arm 254 of the connection portion 204 of the tube unit 94 is engaged with the fixing portion 46a, the tube unit 94 is rotated together with the shaft 34 and the end effector 36 according to the operation of the rotation knob 46.

The handle 32 includes switches 48a and 48b on the housing 42. For example, when a first switch 48a is pressed, a signal is output from the energy source 14 to the fluid source 18, and a fluid (liquid) such as physiological saline is supplied from the fluid source 18 to the tube unit 94 explained later on, and electric power, that is, energy (high-frequency energy), is supplied between electrodes 72 and 82 explained later on from the energy source 14. For example, when one of a second switch 48b, a third switch 48c, and a foot switch (not shown) is pressed, a signal is output from the energy source 14 to the suction source 20a. The suction source 20a then operates to perform suction on the distal end side of the tube main body 212 via the tube main body 212 of the tube unit 94, and stores aspirated material in the suction tank 20b. When the pressed switch among the second switch 48b, the third switch 48c, and the foot switch (not shown) is released, a signal is output to the suction source 20a to stop the operation of the suction source 20a.

In the above explanation, an example of supplying a liquid by electrically controlling the fluid source 18 has been explained. A method of not performing control by the energy source (controller) 14 when supplying the liquid from the fluid source 18 may also be adopted. In this case, the energy source 14 and the fluid source 18 need not be connected.

For example, a liquid pack (fluid source 18), in which a liquid such as physiological saline is stored, is suspended from a suspension stand, and the liquid pack and the tube main body 212 are connected by a tube, a connector, or the like. The physiological saline is then dripped in the same manner as a drip injection by utilizing atmospheric pressure or gravity applied to the liquid pack.

In the above explanation, the suction of the liquid by the suction source 20a is electrically ON/OFF controlled. A method in which the ON/OFF control of the suction is not performed at the suction source 20a may also be adopted. For example, the suction by the suction source 20a may be continued while continuing to drip the physiological saline from the liquid pack, or, the liquid may be suctioned after completion of the treatment without performing the suction by the suction source 20a during the treatment.

Figure 2A:
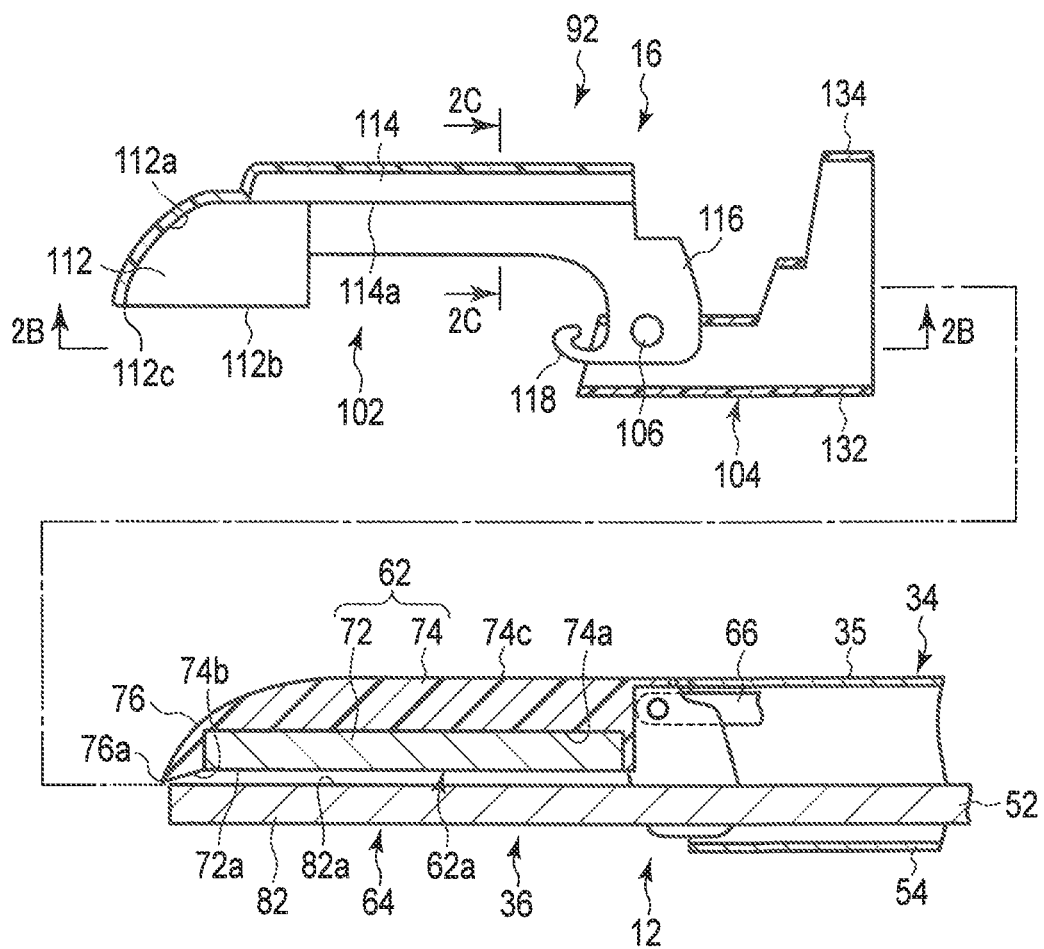
FIG. 2A is a schematic cross-sectional view showing a state in which a fluid supply instrument of a fluid suction/fluid supply unit is to be mounted on a first grasping section of an end effector of a treatment instrument of the treatment system according to the first embodiment.

As shown in FIG. 2A, the shaft 34 includes a rod 52 whose distal end portion is used as a second grasping section 64 (explained later on) of the end effector 36, and a pipe 54 that covers the outer circumferential surface of the rod 52. The distal end of the rod 52 protrudes to the distal end side along the longitudinal axis L with respect to the distal end of the pipe 54. That is, the pipe 54 covers the outer circumferential surface of the rod 52 except for the distal end portion of the rod 52. The proximal end of the rod 52 is supported within the handle 32.

As shown in FIG. 1, the end effector 36 includes a pair of grasping sections 62 and 64. Here, a first grasping section 62, which is one of the pair of grasping sections 62 and 64, is formed to be movable. Since it is publicly-known, explanations will be omitted; however, at a position where the movable handle 44 of the handle 32 is spaced apart from the fixed handle 42a, the movable first grasping section 62 is in an open position (see FIG. 1) where it is spaced apart from the other second grasping section 64 by a link mechanism 66 (see FIG. 2A) which is interlocked with the operation of the movable handle 44. At a position where the movable handle 44 of the handle 32 is close to the fixed handle 42a, the movable first grasping section 62 is in a closed position close to the other second grasping section 64 by the link mechanism 66 (see FIG. 2A).

As shown in FIG. 2A, here, an example in which the end effector 36 of the treatment instrument 12 includes a pair of electrodes 72 and 82, and in which a treatment (for example, sealing a living tissue) is performed on the treatment target using bipolar high-frequency energy, will be explained. In this embodiment, in order to perform treatment (for example, sealing the living tissue) on the treatment target using bipolar high-frequency energy, the first grasping section 62 includes a first electrode 72, and the second grasping section 64 includes a second electrode 82. At least a position of the distal end portion of the rod 52 that faces the first electrode 72 has conductivity. The second electrode 82 includes a grasping surface (electrode surface) 82a which cooperates with a grasping surface 62a of the first electrode 72 to grasp the living tissue of the treatment target. The grasping surface 82a can be visually recognized by a user.

As shown in FIG. 2A, the first grasping section 62 includes the first electrode 72 that faces the second electrode 82 of the second grasping section 64, and includes a movable member 74 which covers a side of the first electrode 72 spaced apart from the second electrode 82. The first electrode 72 and the movable Member 74 are formed so that the direction along the longitudinal axis L is longer than a width direction orthogonal to the longitudinal axis L. Here, the movable member 74 includes a concave portion 74a which fixes the first electrode 72, an edge portion 74b (see FIG. 3B) which is formed outside the concave portion 74a, and a back surface 74c which is continuous to the edge portion 74b and on the opposite side to the side where the first electrode 72 is fixed (concave portion 74a). Normally, the concave portion 74a of the movable member 74 is not visually recognized by the user.

Figure 3A:
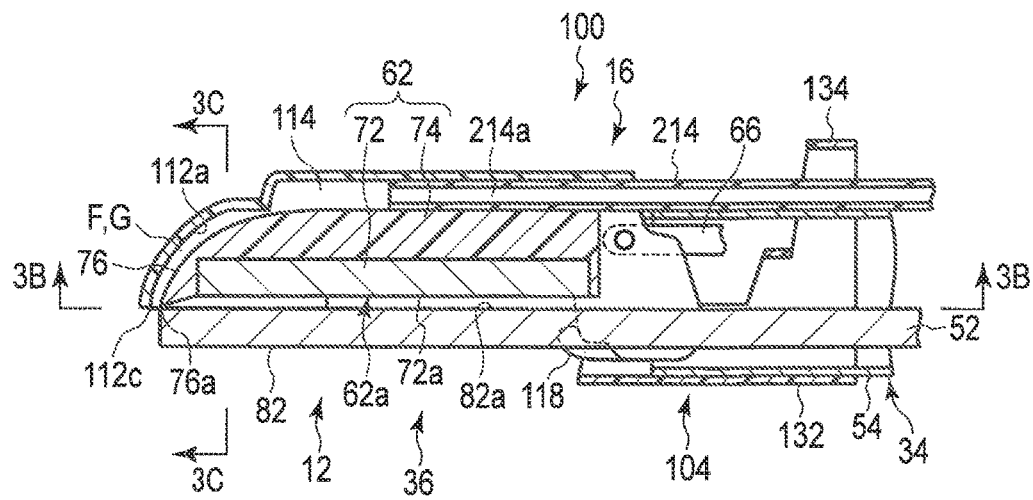
FIG. 3A is a schematic cross-sectional view showing a state in which a treatment instrument unit is configured by mounting the fluid supply instrument of the fluid suction/fluid supply unit on the first grasping section of the end effector of the treatment instrument of the treatment system according to the first embodiment.
Figure 3B:
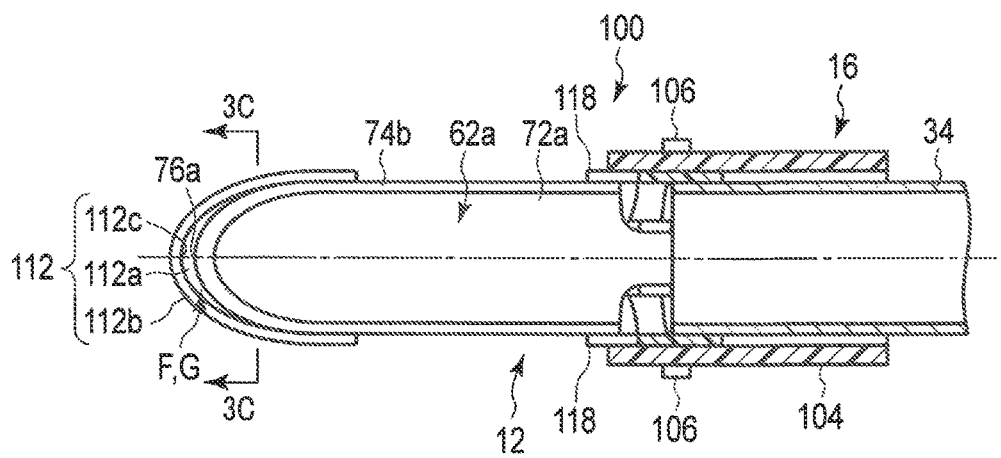
FIG. 3B is a schematic view of a state in which the treatment instrument unit configured by mounting the fluid supply instrument of the fluid suction/fluid supply unit on the first grasping section of the end effector of the treatment instrument of the treatment system according to the first embodiment is viewed from a position taken along a line 3B-3B in FIG. 3A.

As shown in FIG. 2A and FIG. 3B, the first electrode 72 includes an electrode surface 72a that comes in contact with the living tissue to be treated. The edge portion 74b of the movable member 74 and the electrode surface 72a of the first electrode 72 cooperate to form the grasping surface 62a which is configured to grasp the living tissue to be treated. The grasping surface 62a can be visually recognized by the user.

It is preferable that the back surface 74c of the movable member 74 shown in FIG. 2A be formed into a smoothly curved surface shape that prevents the living tissue from being caught. The back surface 74c of the movable member 74 is formed into a curved surface shape, in which the height and the width with respect to the grasping surface 62a decrease toward the distal end indicated by symbol 76a. Normally, the back surface 74c of the movable member 74 forms a part of the outer surface of the first grasping section 62, which is easily visually recognized by the user and is easily touched by the user.

In the case where the first grasping section 62 is in the closed position with respect to the second grasping section 64, the first electrode 72 is close to the second electrode 82. It is preferable that even if the first grasping section 62 is in the closed position with respect to the second grasping section 64, and the first electrode 72 is close to the second electrode, the first electrode 72 and the second electrode 82 are configured to be separated from each other.

The fluid suction/fluid supply unit 16 shown in FIG. 1 includes a fluid supply instrument (liquid supply instrument) 92 for the treatment instrument 12 that defines a fluid channel F to the living tissue to be treated in cooperation with the first grasping section 62 of the end effector 36 of the treatment instrument 12, and the tube unit 94 that is configured to supply a fluid (liquid) to the fluid supply instrument 92. That is, since the fluid supply instrument 92 is mounted on the first grasping section 62 of the treatment instrument 12 capable of grasping the living tissue, an assembly of the treatment instrument 12 and the fluid supply instrument 92 is used as the treatment instrument unit 100.

If it is only necessary to supply fluid to the fluid supply instrument 92, a small-diameter flexible tube may be used as the tube unit 94. In this embodiment, the tube unit 94 is explained as including a plurality of lumens (channels) capable of supplying and suctioning fluid. The tube unit 94 according to this embodiment is used by being attached to the shaft 34 of the treatment instrument 12 and the rotation knob 46 of the handle 32. The fluid supply instrument 92 and the tube unit 94 are used in combination. The fluid supply instrument 92 and the tube unit 94 may be integrated when being mounted on the treatment instrument 12, or may be separated from each other.

As described above, the fluid supply instrument 92 shown in FIG. 1 to FIG. 4 is mounted on the treatment instrument 12 and used as the treatment instrument unit 100. As shown in FIG. 2A and FIG. 2B, the fluid supply instrument 92 includes a main body (mounting body) 102 that can be mounted on the first grasping section 62, and a support section 104 that is supported in a state of being mounted on the distal end portion of the shaft 34. The main body 102 is rotatable via a pin 106 with respect to the support section 104. That is, the support section 104 is attached to the treatment instrument 12, and pivotally supports a cover 112, explained later on, so as to be rotatable in accordance with the rotation of the first grasping section 62. It is preferable that the pin 106 that is the rotation center of the support section 104 with respect to the main body 102 of the fluid supply instrument 92 coincides with the rotation center of the first grasping section 62 with respect to the shaft 34 of the end effector 30 of the treatment instrument 12.

As shown in FIG. 2A to FIG. 4, the main body 102 includes a cup-shaped cover 112 which is configured to cover a distal end portion 76 of the back surface 74c of the movable member 74 of the first grasping section 62, and a port (channel) 114 which is configured to receive fluid from the outside. The cover 112 is continuous with the port 114 and defines a fluid channel F of a fluid such as a liquid supplied from the outside of the fluid supply instrument 92. The cover 112 forms a fluid channel F continuous from the port 114 in cooperation with the first grasping section 62, and allows the fluid received from the port 114 to flow out from between a cover edge 112b, explained later on, of the cover 112 adjacent to the grasping surface 62a and the edge portion 74b of the grasping surface 62a.

The main body 102 includes a pair of connection sections 116 connected to the support section 104 via a pair of pins 106. The connection sections 116 are formed on the proximal end side with respect to the cover 112 along the longitudinal axis L. The connection sections 116 are located adjacent to the proximal end of the port 114. The pair of connection sections 116 are separated from each other. A pair of holding arms (holding portion) 118 which is configured to hold the vicinity of the proximal end portion of the movable member 74 of the first grasping section 62 is provided on the pair of connection sections 116. The holding arms 118 are elastically deformable and urge the hack surface 74c of the first grasping section 62 and an edge portion 114a, explained later on, of the port 114 so as to be in close contact with each other.

Figure 4:
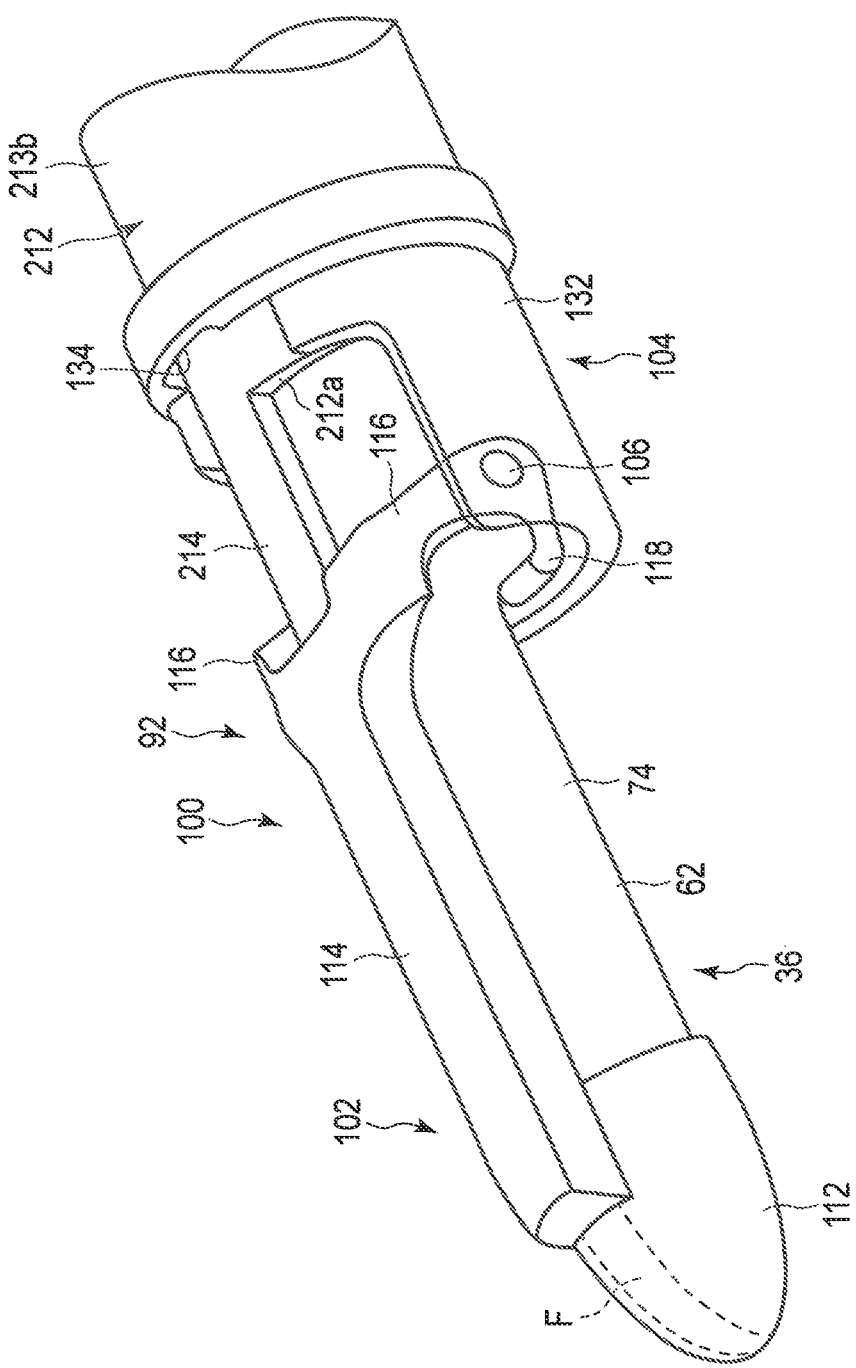
FIG. 4 is a schematic perspective view showing a state in which the treatment instrument unit is configured by mounting the fluid suction/fluid supply unit on the first grasping section of the treatment instrument of the treatment system according to the first embodiment.

As shown in FIG. 3A, FIG. 3B, and FIG. 4, when the fluid supply instrument 92 is mounted on the treatment instrument 12, the holding arms 118 hold the vicinity of the proximal end portion of the movable member 74 so that the main body 102 is attached to the movable member 74 of the first grasping section 62. Therefore, as the first grasping section 62 moves to the open position (see FIG. 1), the main body 102 rotates with respect to the support section 104 via the pin 106. Similarly, as the first grasping section 62 moves to the closed position (see FIG. 3A), the main body 102 rotates with respect to the support section 104 via the pin 106. That is, the holding arms (holding portion) 118 hold the state in which the cover 112 and the port 114 rotate together with the first grasping section 62. The pin 106 may be formed integrally with the main body 102, or may be integrally formed with the support section 104.

Figure 2B:
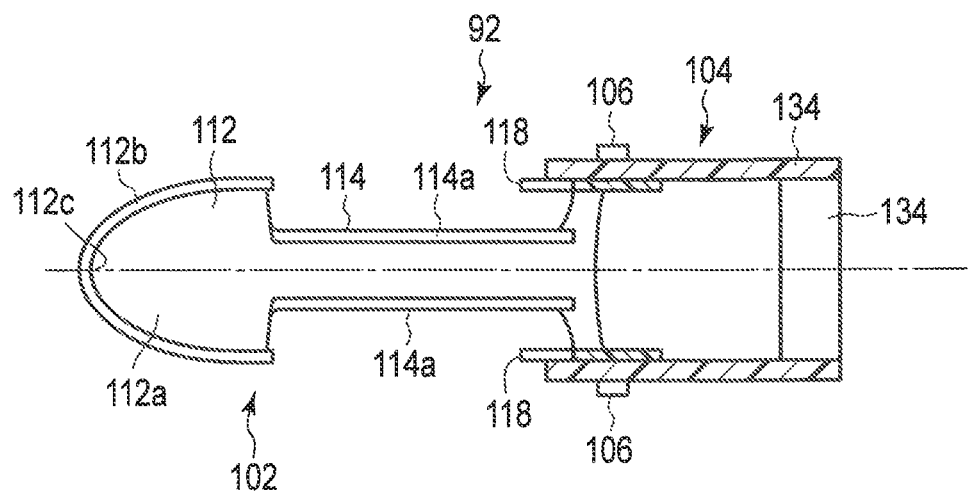
FIG. 2B is a schematic partial cross-sectional view showing a state in which the fluid supply instrument of the fluid suction/fluid supply unit of the treatment system according to the first embodiment is viewed from a position taken along a 2B-2B line in FIG. 2A.

As shown in FIG. 2A and FIG. 2B, it is preferable that the cover 112, the port 114, the pair of connection sections 116, and the pair of holding arms 118 are integrally formed.

As shown in FIG. 2A, FIG. 2B, and FIG. 3A to FIG. 4, the cover 112 has an inner circumferential surface 112a that is configured to cover the vicinity of the distal end portion 76 including the distal end 76a of the back surface 74c of the movable member 74 of the first grasping section 62 of the treatment instrument 12. As shown in FIG. 2A and FIG. 2B, the cover 112 is formed in a substantially quarter-spherical shape. As shown in FIG. 2B, the cover 112 has a substantially U-shaped cover edge 112b at a position facing the second grasping section 64.

As shown in FIG. 3A and FIG. 3B, a position facing the distal end 76a of the back surface 74c of the movable member 74 of the first grasping section 62, indicated by symbol 112c in the cover edge 112b, is separated from the distal end 76a of the back surface 74c of the movable member 74 of the first grasping section 62. Therefore, a gap G is formed between the inner circumferential surface 112a of the cover 112 and the distal end portion 76 of the back surface 74c of the movable member 74 of the first grasping section 62.

Figure 2C:
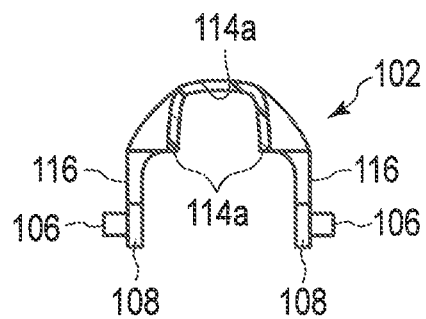
FIG. 2C is a cross-sectional view of the fluid supply instrument of the fluid suction/fluid supply unit of the treatment system according to the first embodiment taken along a 2C-2C line in FIG. 2A.

As shown in FIG. 2A to FIG. 2C, in this embodiment, the port 114 is formed in, for instance, a substantially U-shaped half-pipe shape, with a substantially U-shaped cross section orthogonal to the longitudinal axis L. As shown in FIG. 3A and FIG. 4, a first conduit 214 (explained later on) serving as a fluid supply pipe of the tube unit 94 is fitted to the port 114. For example, it is preferable that the width of the port 114 is gradually reduced from its proximal end side to its distal end side. Therefore, it is easy to maintain the fitting state of the first conduit 214 (explained later on) of the tube unit 94 with respect to the port 114.

As shown in FIG. 1, FIG. 3A, and FIG. 4, the first conduit (liquid supply pipe) 214 (explained later on) of the tube unit 94 is disposed between the pair of connection sections 116.

Figure 3C:
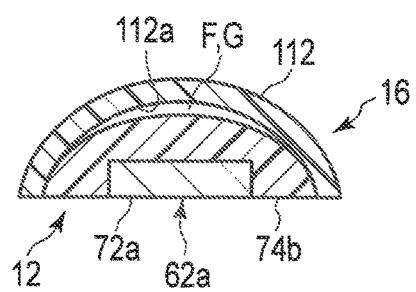
FIG. 3C is a schematic view of a state in which the fluid supply instrument of the fluid suction/fluid supply unit mounted on the first grasping section of the end effector of the treatment instrument of the treatment system according to the first embodiment is viewed from a position taken along a line 3C-3C in FIG. 3A and FIG. 3B.

As shown in FIG. 3A and FIG. 3C, the port 114 forms the fluid channel F of a fluid by the gap G between the port 114 and the back surface 74c of the movable member 74. It is preferable that a portion on the proximal end side of the edge portion 114a of the port 114 is in close contact with the back face 74c of the movable member 74. It is also preferable that a sealing material such as a rubber material is fixed to the edge portion 114a of the port 114 shown in FIG. 2A to FIG. 2C.

As shown in FIG. 3A, in a state where the fluid supply instrument 92 is mounted on the first grasping section 62, the proximal end of the port 114 is kept in close contact with the back surface 74c of the movable member 74, and the distal end of the port 114 is kept separated from the back surface 74c of the movable member 74. Therefore, the distal end of the port 114 communicates with the gap G between the cover 112 and the back surface 74c of the movable member 74 of the first grasping section 62.

The fluid supply instrument 92 forms a gap G from the distal end of the port 114 to the distal end 112c of the cover edge 112b of the cover 112 with respect to the distal end portion 76 of the back surface 74c of the movable member 74 of the first grasping section 62. Therefore, the fluid channel F is defined from the distal end of the port 114 to the distal end 112c of the cover edge 112b of the cover 112.

As shown in FIG. 1 to FIG. 4, the support section 104 may have a cylindrical portion 132 to be fitted to an outer circumferential surface 35 of the shaft 34. A part of the cylindrical portion 132 forms a guide portion 134 that permits the movement of the first conduit 214 of the tube unit 94 and guides the movement. When the first grasping section 62 and the main body 102 of the fluid supply instrument 92 are rotated, the guide portion 134 prevents a load from being applied between the first conduit 214 of the tube 202 of the tube unit 94 and the port 114 of the main body 102 of the fluid supply instrument 92. Accordingly, the fitting between the first conduit 214 of the tube unit 94 and the main body 102 of the fluid supply instrument 92 is maintained. In addition, the state in which the main body 102 of the fluid supply instrument 92 is fitted to the first grasping section 62 is maintained.

If it is guaranteed that the fluid supply instrument 92 will not come off of the first grasping section 62 of the treatment instrument 12 during the treatment of the living tissue in a state where the main body 102 of the fluid supply instrument 92 is mounted on the first grasping section 62, the support section 104 is not necessarily required. In the present embodiment, even if the main body 102 of the fluid supply instrument 92 is unintentionally disengaged from the first grasping section 62, since the state in which the support section 104 is attached to the treatment instrument 12 (shaft 34) is maintained, it is guaranteed that the fluid supply instrument 92 (main body 102) would not-come off of the treatment instrument 12.

As shown in FIG. 1, the tube unit 94 includes a tube 202 which is mounted on the outer side of the pipe 54 of the shaft 34 and used, and a connection portion 204 which is fixed to the proximal end of the tube 202 and is configured to be connected to the rotation knob 46. The tube 202 is made of a flexible material such as a silicone material, a polyurethane material, a polyethylene material, or the like.

Figure 5:
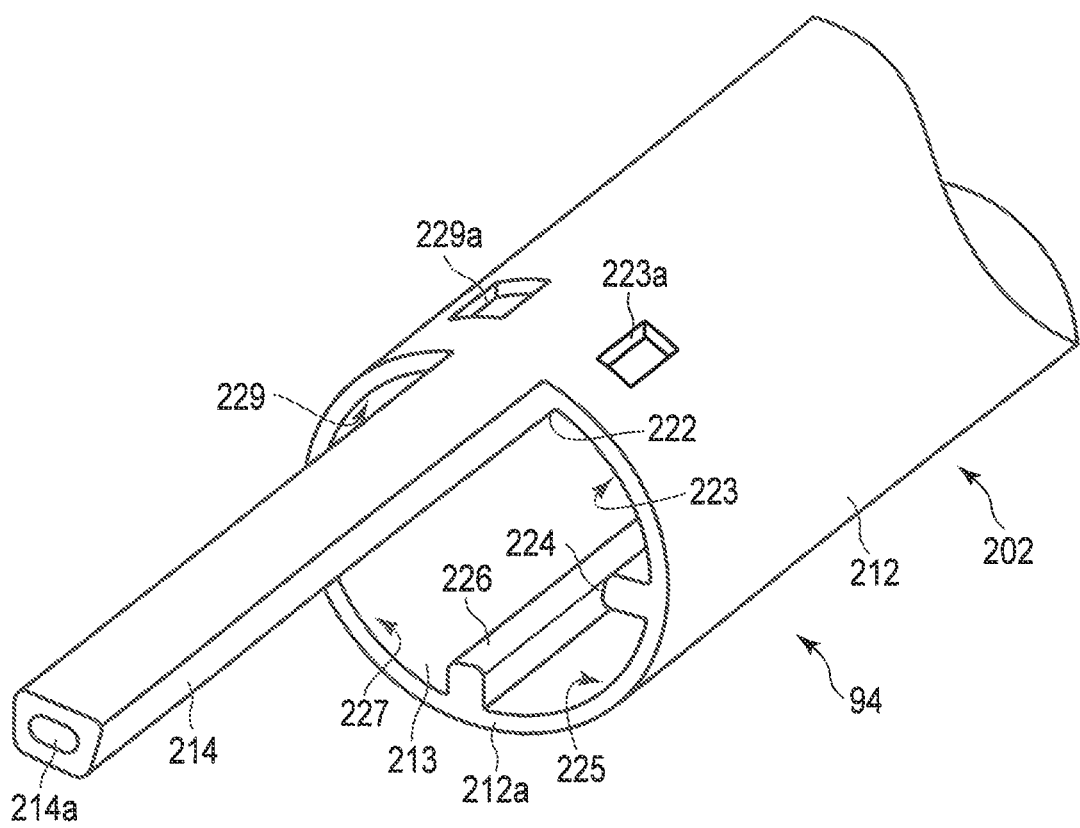
FIG. 5 is a schematic perspective view showing a vicinity of a distal end portion of a tube unit of the fluid suction/fluid supply unit of the treatment system according to the first embodiment.
Figure 6A:
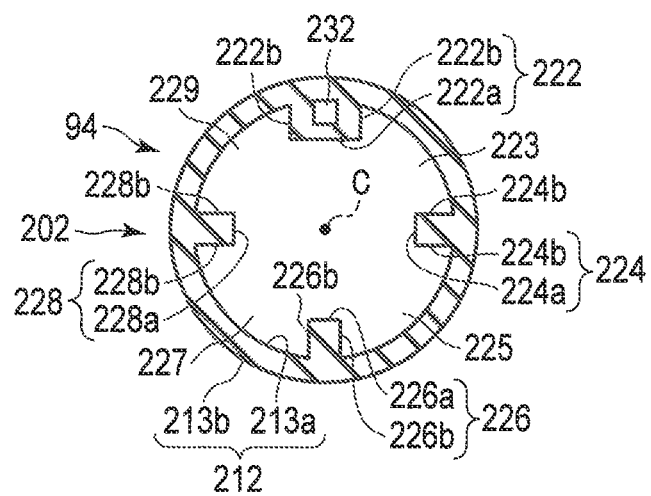
FIG. 6A is a schematic view of a tube main body of the tube unit of the fluid suction/fluid supply unit of the treatment system according to the first embodiment viewed from a position taken along line 6A-6A in FIG. 1.
Figure 6B:
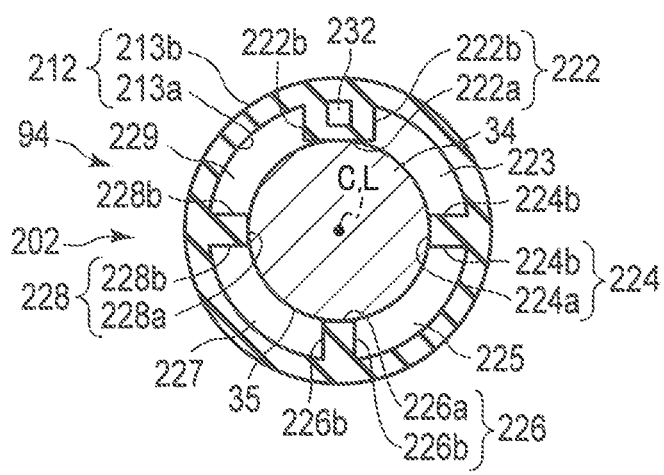
FIG. 6B is a schematic view showing a state in which a shaft is inserted through the tube main body of the tube unit shown in FIG. 6A.

As shown in FIG. 5, the tube 202 includes a tubular main body (outer tube) 212, and a first conduit (distal end side conduit) 214 protruding toward the distal end side from the distal end 212a of the main body 212. The main body 212 extends along a central axis (longitudinal axis) C defined by the distal end 212a and a proximal end 212b (see FIG. 8A). It is preferable that the main body 212 and the first conduit 214 are integrally formed. As shown in FIG. 5, FIG. 6A, and FIG. 6B, the main body 212 has a plurality of (here, four) convex portions (ribs) 222, 224, 226, and 228 protruding inward in a radial direction. The convex portions 222, 224, 226, and 228 are provided along the central axis C.

The convex portions 222, 224, 226, and 228 have convex surfaces 222a, 224a, 226a, and 228a and a pair of side surfaces 222b, 224b, 226b, and 228b, respectively. The convex surfaces 222a, 224a, 226a, and 228a are located at positions protruding inward in the radial direction of the tube main body 212 with respect to an inner circumferential surface 213a of the tube main body 212. The convex surfaces 222a, 224a, 226a, and 228a come in contact with the outer circumferential surface 35 of the shaft 34. Each of the pair of side surfaces 222b, 224b, 226b, and 228b is formed between the convex surfaces 222a, 224a, 226a, and 228a and the inner circumferential surface 213a of the tube main body 212. Each of the pair of side surfaces 222b, 224b, 226b, and 228b is oriented in a direction in which the normal lines are substantially opposite to each other.

It is preferable that the main body 212 and the plurality of convex portions 222, 224, 226, and 228 are integrally formed. It is preferable that the convex portions 222, 224, 226, and 228 are formed at appropriate intervals in the circumferential direction with respect to the central axis C of the main body 212. Here, the convex portions 222, 224, 226, 228 are formed at intervals of 90° in the circumferential direction with respect to the central axis C of the main body 212. It is preferable that the convex portions 222, 224, 226, and 228 are continuously formed from the distal end 212a (see FIG. 5) to the proximal end 212b (see FIG. 8A) of the main body 212 of the tube 202. The distal end 212a of the main body 212 of the tube 202 is used as a suction opening. The proximal end 212b of the main body 212 of the tube 202 is used as a suction guide portion that communicates with a second port 258 in the connection portion 204.

As shown in FIG. 5 to FIG. 6B, a fluid channel (fluid supply pipe line) 232 is formed in one convex portion 222 among the plurality of convex portions 222, 224, 226, and 228. The fluid channel 232 of the convex portion 222 allows a fluid (liquid) flowing in from the proximal end 212b (see FIG. 8A) and flowing out from the distal end 212a of the tube main body 212 to pass through. The fluid channel 232 communicates with a fluid channel 214a of the first conduit 214 protruding from the distal end of the tube 202 to the distal end side.

Figure 8A:
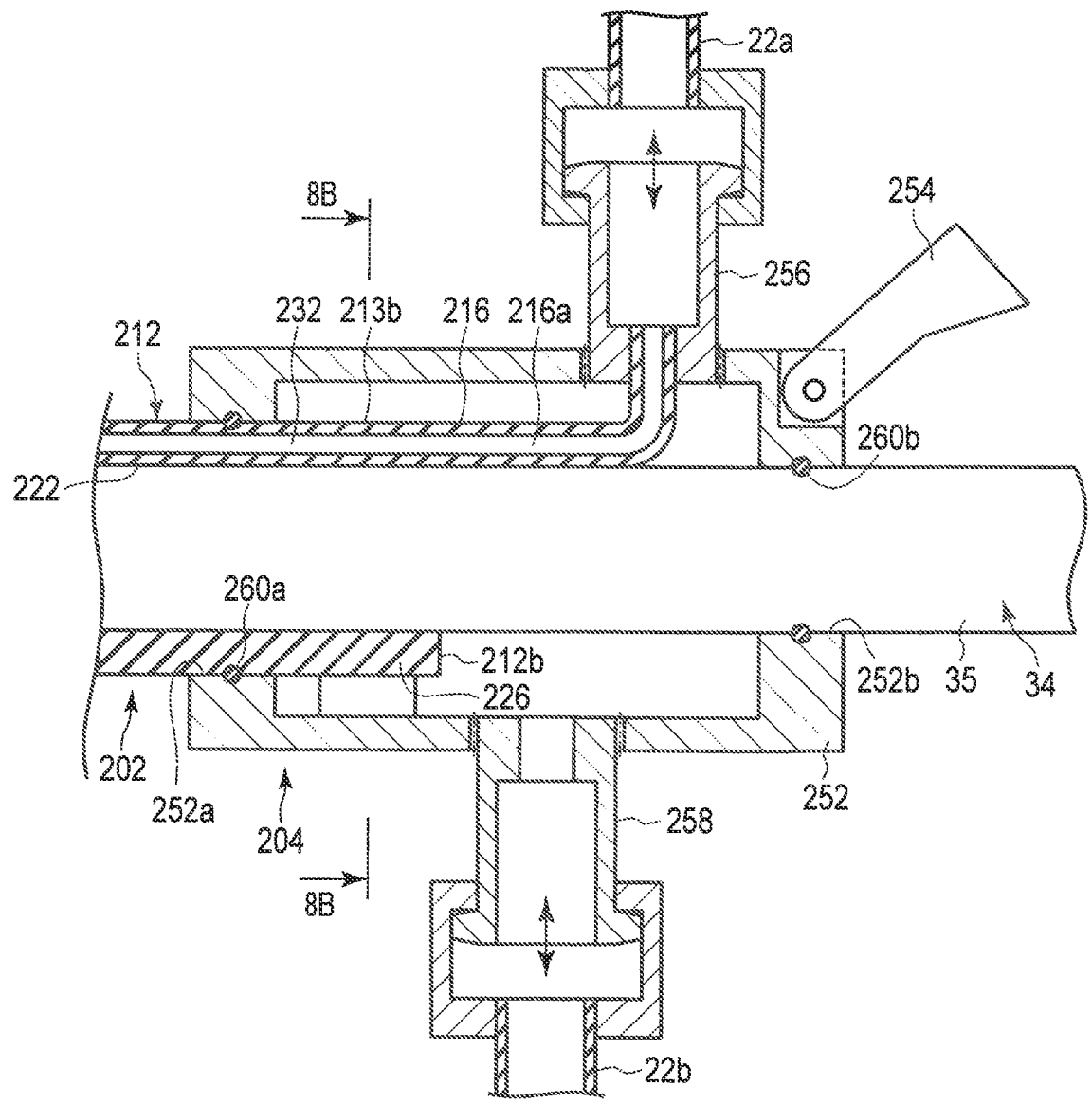
FIG. 8A is a schematic view of an inside of the connection portion showing a state in which the shaft is inserted through the tube main body and the connection portion of the tube unit of the fluid suction/fluid supply unit of the treatment system according to the first embodiment.
Figure 8B:
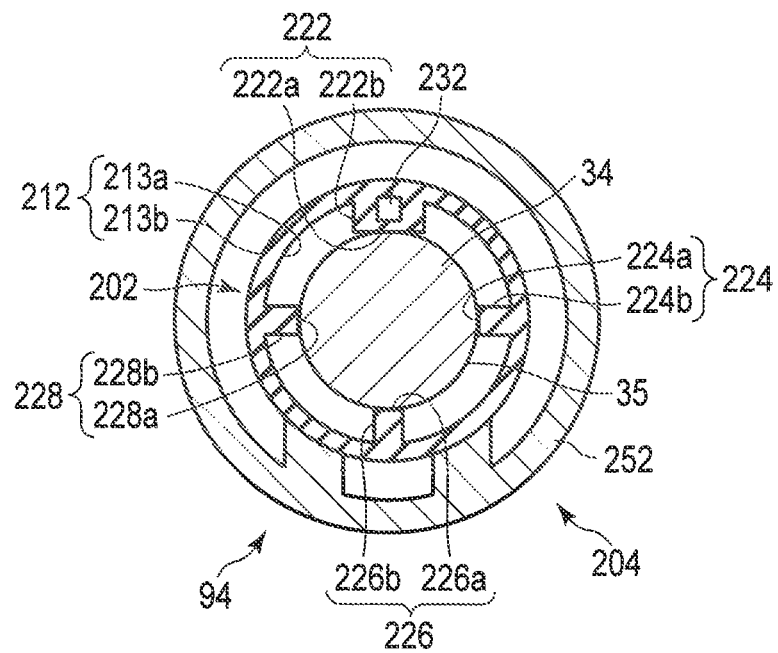
FIG. 8B is a schematic view of the inside of the tube main body and the connection portion in FIG. 8A of the tube unit of the fluid suction/fluid supply unit of the treatment system according to the first embodiment viewed from a position taken along a line 8B-8B.
Figure 9:
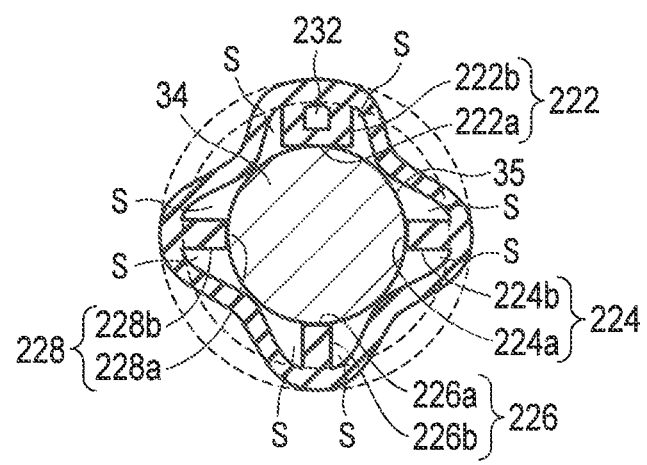
FIG. 9 is a schematic view showing a state in which a space is formed at a position adjacent to each convex portion when a negative pressure is applied to an inside of the tube unit of the fluid suction/fluid supply unit of the treatment system according to the first embodiment, so that an inner circumferential surface of the tube main body approaches or is brought into close contact with an outer circumferential surface of the shaft, in the state where the shaft is inserted through the tube main body of the tube unit shown in FIG. 6A.

As shown in FIG. 8A, in this embodiment, the tube 202 has a second conduit (proximal end side conduit) 216 serving as a fluid supply pipe protruding from the proximal end 212b of the main body 212 to the proximal end side. It is preferable that the main body 212 and the second conduit 216 are integrally formed. The fluid channel 232 communicates with a fluid channel 216a of the second conduit 216. Therefore, a fluid such as a liquid can flow from the fluid channel 216a of the second conduit 216 to the fluid channel 214a of the first conduit 214 through the fluid channel 232 of the main body 212. Therefore, a fluid such as a liquid can flow out from the distal end of the fluid channel 214a of the first conduit 214.

As shown in FIG. 6B, in a state where the shaft 34 of the treatment instrument 12 is disposed inside the tube 202, lumens 223, 225, 227, and 229 are formed respectively between the convex portions 222 and 224, the convex portions 224 and 226, the convex portions 226 and 228, and the convex portions 228 and 222. That is, the main body 212 of the tube unit 94 cooperates with the shaft 34 of the treatment instrument 12 to form a plurality of lumens 223, 225, 227, and 229.

The convex portion 222 cooperates with the inner circumferential surface 213a of the tube main body 212 and the outer circumferential surface 35 of the shaft 34 to form the lumens 223 and 229 at positions adjacent to each other in the circumferential direction. The convex portion 224 forms the lumens 223 and 225 at positions adjacent to each other in the circumferential direction. The convex portion 226 forms the lumens 225 and 227 at positions adjacent to each other in the circumferential direction. The convex portion 228 forms the lumens 227 and 229 at positions adjacent to each other in the circumferential direction.

As shown in FIG. 5, the tube main body 212 has through-holes 223a and 229a which are configured to penetrate the inner circumferential surface 213a and an outer circumferential surface 213b at the vicinity of the distal end 212a. When clogging occurs at the distal end of each of the lumens 223 and 229 shown in FIG. 5, suction is performed from the through-holes 223a and 229a formed on the side surface of the main body 212. It is, of course, preferable that through-holes (not shown) are also formed for the lumens 225 and 227.

As shown in FIG. 7A to FIG. 8B, the connection portion 204 includes a tubular main body (housing) 252, the fixing arm (fixing portion) 254, a first port (fluid supply port) 256, and the second port (suction port) 258. On the main body 252, at the distal end of the main body 252 is formed a first through-hole 252a into which the tube main body 212 is inserted, and at the proximal end of the main body 252 is formed a second through-hole 252b through which the shaft 34 is inserted. As a first seal member, an O-ring 260a is disposed at an edge portion of the first through-hole 252a, and, as a second seal member, an O-ring 260b is disposed at an edge portion of the second through-hole 252b. The O-ring 260a on the distal end side is brought into close contact with the outer circumferential surface 213b of the main body 212 of the tube 202. That is, the first seal member 260a seals between the outer circumferential surface 213b of the tube main body 212 and the main body 252 of the connection portion 204. The O-ring 260b on the proximal end side is brought into close contact with the outer circumferential surface 35 of the shaft 34 of the treatment instrument 12. That is, the second seal member 260b seals between the outer circumferential surface 35 of the shaft 34 and the main body 252 of the connection portion 204.

The first port 256 is provided on the main body 252 of the connection portion 204, and communicates with the second conduit 216 of the tube 202. In this embodiment, the first port 256 is used for fluid supply. The first port 256 is connected to the fluid source 18 shown in FIG. 1 via a tube 22a. The first port 256 may also be used for air supply.

The second port 258 is provided on the main body 252 of the connection portion 204, and communicates with the inner side and the outer side of the main body 252. The proximal end 212b of the main body 212 of the tube 202 communicates with the second port 258 inside the main body 252 of the connection portion 204. That is, the second port 258 communicates with the proximal end 212b of the tube main body 212. The second port 258 is used for suction in this embodiment. The second port 258 is connected to the suction tank 20b shown in FIG. 1 via a tube 22b.

Figure 7A:
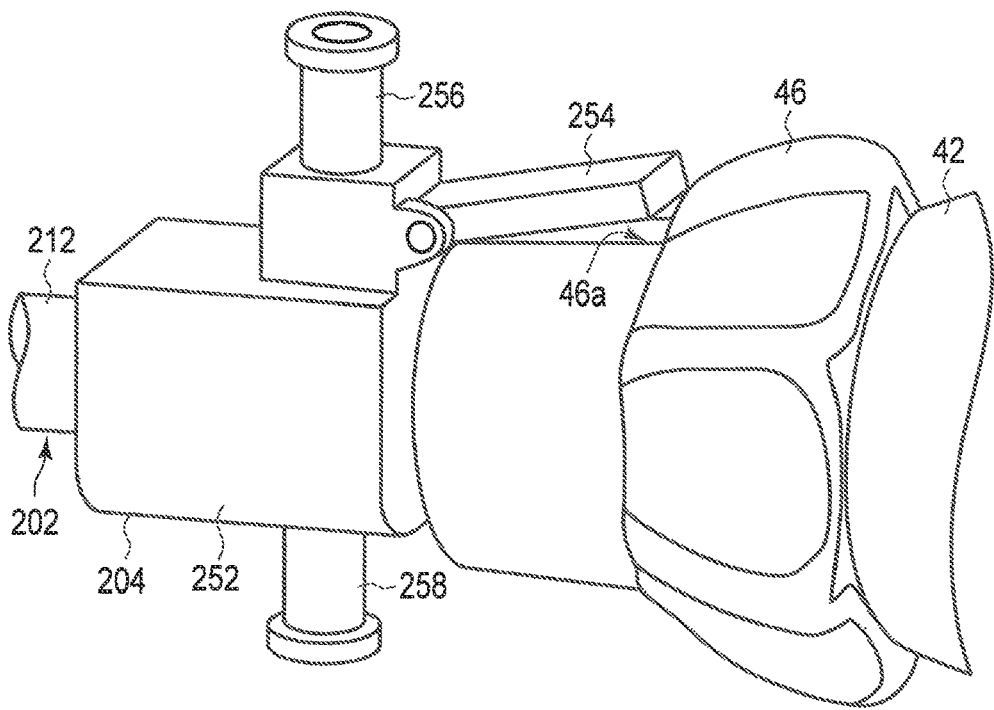
FIG. 7A is a schematic view showing a state in which a fixing arm of a connection portion of the tube unit of the fluid suction/fluid supply unit of the treatment system according to the first embodiment is to be fitted into a concave portion of a rotation knob of the treatment instrument.
Figure 7B:
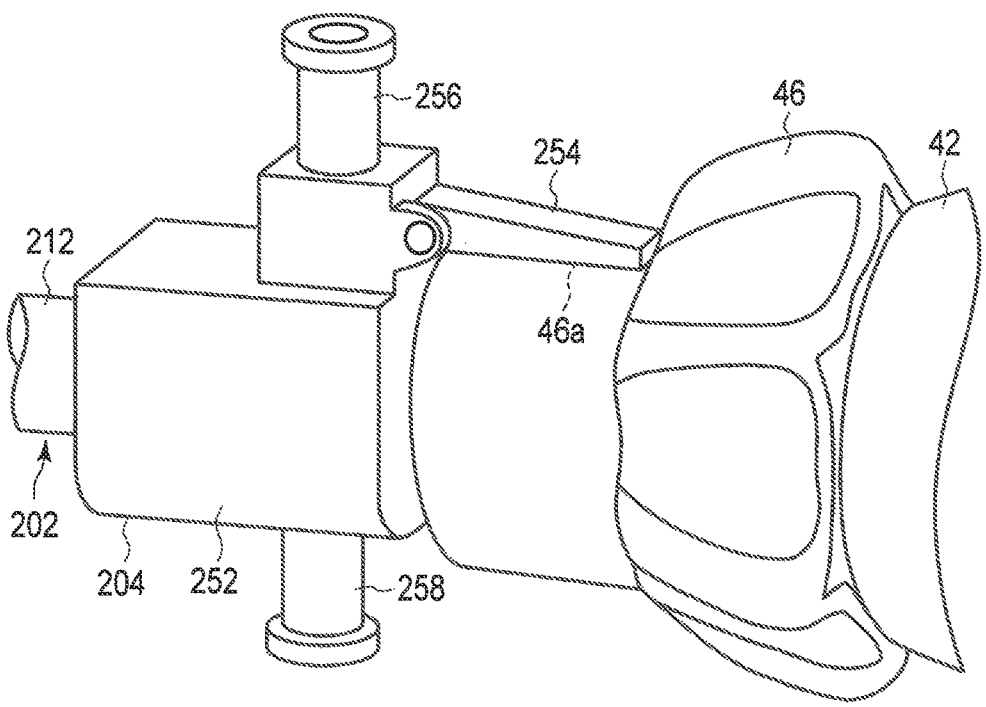
FIG. 7B is a schematic view showing a state in which the treatment instrument unit is configured by fitting, to the concave portion of the rotation knob of the treatment instrument, the fixing arm of the connection portion of the tube unit of the fluid suction/fluid supply unit of the treatment system according to the first embodiment.

As shown in FIG. 7A and FIG. 7B, the fixing arm 254 is fixed to the concave fixing portion 46a of the rotation knob 46. For example, if there is only one fixing arm 254, and one fixing portion 46a corresponding to the fixing arm 254, the orientation of the fluid suction/fluid supply unit 16 is determined. At this time, the fixing arm 254 is fixed with respect to the rotation knob 46, which is with respect to both the direction along the longitudinal axis L and the direction about the axis of the longitudinal axis L. Therefore, when the rotation knob 46 is rotated about the axis of the longitudinal axis L in a state where the fixing arm 254 is fixed to the rotation knob 46, the tube 202 on the outer side of the shaft 34 also rotates.

As shown in FIG. 1, the treatment instrument 12, the energy source 14, the fluid source 18, and the suction source 20a are capable of transmitting and receiving electric signals. Therefore, when the switch 48a is pressed, a signal is transmitted from the energy source 14 to the fluid source 18, which drives the fluid source 18, and a high-frequency energy is output from the energy source 14. Furthermore, when the switch 48b is pressed, a signal is transmitted from the energy source 14 to the suction source 20a, and the suction source 20a is driven.

The flow rate per unit of time of the fluid supplied from the fluid source 18 when the switch 48a of the treatment instrument 12 is pressed, the length of the fluid channels 216a, 232, and 214a of the tube unit 94, and the cross-sectional area of the fluid channels 216a, 232, and 214a, etc. are inputted to the energy source 14 as appropriate. And, the time from pressing the switch 48a to outputting the high-frequency current from the energy source 14 is set. Therefore, a timing at which the fluid flows out to the grasping surface 62a of the first grasping section 62 of the end effector 36, and a timing at which the high-frequency current is output can be adjusted. In addition, a high-frequency current may be outputted after recognizing that the fluid has passed through an appropriate position of the tube unit 94 by a sensor or the like.

In the case of supplying a liquid by the fluid source 18 using a liquid pack that does not electrically control the liquid supply, the liquid pack containing a liquid such as physiological saline is suspended from a suspension stand. The liquid pack and the tube main body 212 are connected by a tube, a connector or the like, and the physiological saline is dripped in the same manner as the drip infusion using atmospheric pressure or gravity applied to the liquid pack. Although not shown, if an adjustment device is attached to the tube for adjusting the flow rate of the liquid flowing through the tube by pressing the tube to deform the tube, the flow rate of the liquid to be dropped can be appropriately adjusted by an operator adjusting the adjustment device.

The operation of the treatment system 10 according to the embodiment will now be explained. Here, an example of using physiological saline as the liquid supplied from the fluid source 18 will be explained. In addition, here, an example of coagulating/sealing a living tissue to be treated using a high-frequency current (high-frequency energy) as an energy for treating the living tissue will be explained. As the living tissue to be treated, an example of a blood vessel will be described.

The first conduit 214 of the tube unit 94 is fitted from the proximal end side of the port 114 of the main body 102 of the fluid supply instrument 92 shown in FIG. 2A to create the fluid suction/fluid supply unit (auxiliary tool) 16 shown in FIG. 1. At this time, the first conduit 214 of the tube unit 94 passes inside the support section 104 of the fluid supply instrument 92. The fluid suction/fluid supply unit 15 may also be created by fixing the first conduit 214 of the tube unit 94 to the main body 102 of the fluid supply instrument 92 by adhesion or welding.

As shown in FIG. 1, the end effector 36 of the treatment instrument 12 faces the through-hole 252b on the proximal end side of the connection portion 204 of the tube unit 94.

The movable handle 44 of the handle 32 is brought close to the fixed handle 42a to move the first grasping section 62 to the closed position with respect to the second grasping section 64. In this state, the end effector 36 of the treatment instrument. 12 is projected on the distal end side of the distal end 212a of the tube main body 212 through the connection portion 204 and the tube main body 212 of the tube unit 94. At this time, the longitudinal axis L of the treatment instrument 12 coincides with the central axis (longitudinal axis) C of the tube unit 94. As shown in FIG. 3A to FIG. 4, the inner circumferential surface 112a of the cover 112 of the fluid supply instrument 92 is faced to the distal end portion 76 of the back surface 74c of the movable member 74 of the first grasping section 62 of the and effector 36. At this time, the holding arms 118 of the main body 102 of the fluid supply instrument 92 hold the vicinity of the proximal end portion of the movable member 74 of the first grasping section 62 by snap fitting. Therefore, the main body 102 of the fluid supply instrument 92 is attached to the movable member 74 of the first grasping section 62.

When the inner circumferential surface 112a of the cover 112 of the fluid supply instrument 92 is faced to the back surface 74c of the movable member 74 of the first grasping section 62 of the end effector 36, the first conduit 214 of the tube unit 94 is fixed to the back face 74c of the movable member 74 of the first grasping section 62 in a state of being disposed in the port 114 of the fluid supply instrument 92. At this time, the distal end of the port 114 and the distal end of the first conduit 214 are separated. The gap G, that is, the fluid channel F is formed between the vicinity of the distal end of the port 114 and the back face 74c of the movable member 74.

The operator appropriately operates the movable handle 44 and confirms the following operation of the main body 102 of the fluid supply instrument 92 with respect to the movable member 74 of the first grasping section 62.

In the tube unit 94, the proximal end of the main body 252 of the connection portion 204 come into contact with or comes close to the distal end of the rotation knob 46. In this state, as shown in FIG. 7A and FIG. 7B, the fixing arm 254 of the connection portion 204 is fitted into the fixing portion 46a of the rotation knob 46, thereby fixing the fixing arm 254 to the rotation knob 46. Therefore, when the rotation knob 46 is rotated, the connection portion 204 of the tube unit 94 rotates following the rotation of the rotation knob 46.

In a state where the fluid suction/fluid supply unit 16 is attached to the treatment instrument 12, the operator arranges the end effector 36 in a body cavity. The position and posture of the end effector 36 are confirmed using, for example, an endoscope (not shown).

The operator appropriately operates the movable handle 44 to grasp a blood vessel using the distal end portion (the region on the distal end side) of the grasping surface 62a of the first grasping section 62. Subsequently, when the operator presses the first switch 48a, a fluid (liquid) is supplied from the fluid source 18 to the main body 102 of the fluid supply instrument 92 through the tube 22a, the first port 256, and the tube 202, and high-frequency electrical energy is supplied from the energy source 14 to between the electrodes 72 and 82 of the grasping sections 62 and 64.

The fluid is discharged from the distal end of the first conduit 214 toward the distal end of the port 114 of the fluid supply instrument 92. The distal end of the port 114 communicates with the gap G between the inner circumferential surface 112a of the cover 112 and the distal end portion 76 of the back surface 74c of the movable member 74 of the first grasping section 62.

Here, the fluid supply instrument 92 forms the gap G, that is, the fluid channel F, from the distal end of the port 114 to the distal end 112c of the cover edge 112b of the cover 112 with respect to the distal end portion 76 of the back surface 74c of the movable member 74 of the first grasping section 62. Therefore, the fluid flows through the fluid channel F (the gap G). In particular, since the height of the back surface 74c of the movable member 74 with respect to the grasping surface 62a decreases toward the distal end indicated by symbol 76a, the fluid tends to flow toward the distal end 76a of the distal end portion 76 of the back surface 74c of the movable member 74. The fluid passes between the distal end portion 75 of the back surface 74c of the movable member 74 of the first grasping section 62 and the inner circumferential surface 112a of the cover 112 of the fluid supply instrument 92, and is discharged to the grasping surface 62a from between the distal end 76a of the back surface 74c of the movable member 74 of the first grasping section 52 and the cover edge 112b of the cover 112. In this embodiment, physiological saline flows from the distal end of the grasping surface 62a of the first grasping section 62 to the blood vessel to be treated. In other words, in the fluid suction/fluid supply unit 16 and the treatment instrument unit 100 according to this embodiment, the position at which the physiological saline flows into the blood vessel is at the distal end of the grasping surface 62a of the first grasping section 62. In this manner, the fluid channel F between the cover 112 and the back surface 74c of the movable member 74 of the first grasping section 62 of the treatment instrument 12, is formed between the distal end 112c of the cover edge 112b of the cover 112 adjacent to the grasping face 62a and the edge portion 74b of the grasping face 62a. Therefore, the fluid (liquid) is made to flow out from between the distal end 112c of the cover 112 and the edge portion 74b of the grasping surface 62a.

As described above, the treatment system 10 according to this embodiment treats the treatment target of the living tissue by using the high-frequency energy while causing a fluid (liquid) such as physiological saline to flow out and be applied to the treatment target of the living tissue. The physiological saline is made to flow only to the distal end of the grasping surface 62a of the first grasping section 62 where the living tissue to be treated is grasped. Therefore, energy is efficiently supplied to the portion of the living tissue to be treated, to which the physiological saline is applied.

In the grasped blood vessel, the protein is denatured and sealed by the action of the physiological saline and the high-frequency energy. At this time, the grasped blood vessel is prevented from sticking to the grasping surface 62a by the action of the physiological saline. Therefore, for example, when releasing the movable handle 44 to move the first grasping section 62 to the open position with respect to the second grasping section 64, the sealed state of the blood vessel is maintained. In addition, when high-frequency energy is applied to the blood vessel, carbonization of the grasped blood vessel is prevented by the action of the physiological saline.

When the physiological saline flows over the entire surface of the grasping surface 62a of the first grasping section 62, energy is also used at a portion of the living tissue that is not grasped. As in this embodiment, by the physiological saline flowing from the distal end (the distal end of the movable member 74) of the grasping surface 62a of the first grasping section 62 to the living tissue to be treated, the energy can be effectively applied to the living tissue to be treated. Therefore, even if the same energy is used, energy can be used more efficiently by applying the physiological saline only to the distal end 76a of the grasping surface 62a of the first grasping section 62, rather than applying the physiological saline to the entire surface of the grasping surface 62a of the first grasping section 62. Therefore, even if the same energy is used, hemostasis of a blood vessel can be performed quickly and reliably by applying the physiological saline only to the distal end 76a of the grasping surface 62a of the first grasping section 62, rather than applying the physiological saline to the entire surface of the grasping surface 62a of the first grasping section 62.

Here, an example in which the gap G is formed at the distal end 112c of the cover edge 112b with respect to the distal end portion 76 of the back surface 74c of the movable member 74 of the first grasping section 62 has been explained. The position denoted by symbol 112c, that is, the opening of the gap G, may be formed at any position of the cover edge 112b. Although it is preferable that the position denoted by symbol 112c is at the distal end of the cover 112, it may be formed at any position of the cover edge 112b of the cover 112. Even in the case of performing hemostasis in other living tissues such as hepatocytes, in a similar manner as the case of sealing blood vessels, the living tissue to be treated is grasped using the distal end portion (the region on the distal end side) of the grasping surface 62a of the first grasping section 62. Furthermore, the liver has high blood vessel density, and thin blood vessels are distributed at high density. In the case where it is difficult for the first grasping section 62 and the second grasping section 64 to grasp a thin blood vessel appearing while the treatment is being applied to the liver cells, the first grasping section 62 is first opened with respect to the second grasping section 64 to come in contact with the living tissue in a manner that the treatment target is positioned between the first grasping section 64 and the second grasping section 64. The physiological saline is then made to flow from the distal end (the distal end of the movable member 74) of the grasping surface 62a of the first grasping section 62 to the living tissue to be treated, and the first grasping section 62 and the second grasping section 64 are electrically connected via the physiological saline. A high-frequency current is then output, which flows to the treatment target through the physiological saline, and allows hemostasis to be performed on the blood vessel.

In this embodiment, four lumens 223, 225, 227, and 229 are formed between the outer circumferential surface 35 of the shaft 34 and the inner circumferential surface 213a of the main body 212 of the tube unit 94. When the suction source 20a of the fluid suction apparatus 20 applies suction to the second port 258 of the connection portion 204, the pressure is reduced between the inner circumferential surface 213a of the tube main body 212 and the outer circumferential surface 35 of the shaft 34. At this time, the outer circumferential surface 35 of the shaft 34 is formed of a hard material such as a stainless steel material. As described above, the tube main body 212 is formed of a flexible soft material such as a silicone material, a polyurethane material, a polyethylene material or the like. Therefore, when a suction force is exerted between the outer circumferential surface 35 of the shaft 34 and the inner circumferential surface 213a of the tube main body 212, the inner circumferential surface 213a of the tube main body 212 between the convex portions (ribs) 222 and 224, the convex portions 224 and 226, the convex portions 226 and 228, and the convex portions 228 and 222, respectively comes close to or comes into contact with the outer circumferential surface 35 of the shaft 34. As the inner circumferential surface 213a of the tube main body 212 comes close to or comes into contact with the outer circumferential surface 35 of the shaft 34, the convex surfaces 222a, 224a, 226a, and 228a of the convex portions 222, 224, 226, and 228 are brought into close contact with the outer circumferential surface 35 of the shaft 34. At this time, the convex portions 222, 224, 226, and 228 maintain their shapes. That is, the convex portions 222, 224, 226, and 228 maintain the distance (that is, an inward protruding length) between the inner circumferential surface 213a of the tube main body 212 and the convex surfaces 222a, 224a, 226a, and 228a in a state where a negative pressure is applied to the inner side of the tube main body 212.

Therefore, even if a part of the inner circumferential surface 213a of the tube main body 212 is brought into close contact with the outer circumferential surface 35 of the shaft 34 by the suction force, spaces S are maintained at each position adjacent to the pair of side surfaces 222b, 224b, 226b, and 228b of the convex portions 222, 224, 226, and 228 on the inner circumferential surface 213a of the tube main body 212. That is, when the negative pressure is applied to the inner side of the tube main body 212, the Space S is formed, respectively, by the pair of side surfaces 222b, 224b, 226b, and 228b and the inner circumferential surface 213a of the tube main body 212, therebetween the outer circumferential surface 35 of the shaft 34. Therefore, the space S is maintained as a suction channel, and the physiological saline, blood, and living tissue are guided from the distal end 212a to the proximal end 212b of the tube main body 212 by suction, and are discharged to the suction tank 20b through the second port 258 and the tube 22b.

At this time, the inner circumferential surface 213a of the tube main body 212 forms a plurality of lumens 223, 225, 227, and 229 between the inner circumferential surface 213a and the outer circumferential surface 35 of the shaft 34. Therefore, the tube main body 212 only needs to have the inner circumferential surface 213a to form the lumens 223, 225, 227, and 229, which will suppress the increase wall thickness of the tube main body 212.

Furthermore, for example, even if one lumen 223 is communication between the distal end 212a and the proximal end 2 is ensured for the remaining lumens 225, 227, and 229. Therefore, the tube main body 212 can secure the suction channel.

In the body cavity, for example, the separated biological tissue is taken out from the body cavity by using forceps, or by suctioning and removing physiological saline and blood. In addition, when the physiological saline is used in the manner mentioned above, misting may occur, which may interfere with visual recognition of the end effector 36 with the endoscope. In such case, by operating the second switch 48b to perform suction, it is possible to eliminate the operation of grasping the living tissue with the forceps and taking it outside from the body cavity. In addition, it is possible to rapidly remove the mist generated by the treatment or the like.

As explained above, according to the treatment system 10 of this embodiment, the following can be said.

By using the treatment instrument unit 100 in which the fluid supply instrument 92 is mounted on the treatment instrument 12, a fluid (liquid) such as the physiological saline can be dropped to a desired position of the first grasping section 62 through the fluid channel F formed between the fluid supply instrument 92 and the first grasping section 62 of the treatment instrument 12. Therefore, it is possible to treat the living tissue using energy. Therefore, it is possible to perform treatment by efficiently applying energy to the treatment target while discharging the fluid and reducing energy loss.

In addition, suction can be performed using the tube unit 94 in cooperation with the treatment instrument 12. When doing so, the tube unit 94 can cooperate with the treatment instrument 12 to form a plurality of lumens. In particular, even if a negative pressure is applied to the inside of the tube main body 212, since the shapes of the convex portions 222, 224, 226, and 228 are maintained, each of the spaces S can be formed at positions adjacent to the convex portions 222, 224, 226, and 228. Each of the spaces S can then be used as a suction channel. Therefore, it would be unnecessary to carry out an operation such as temporarily taking out the treatment portion of the treatment instrument outside the body to secure the suction channel in order to solve clogging of the suction channel. Therefore, by using the tube unit 94 according to this embodiment, it is possible to efficiently store the aspirated material in the suction tank 20b.

Figure 10:
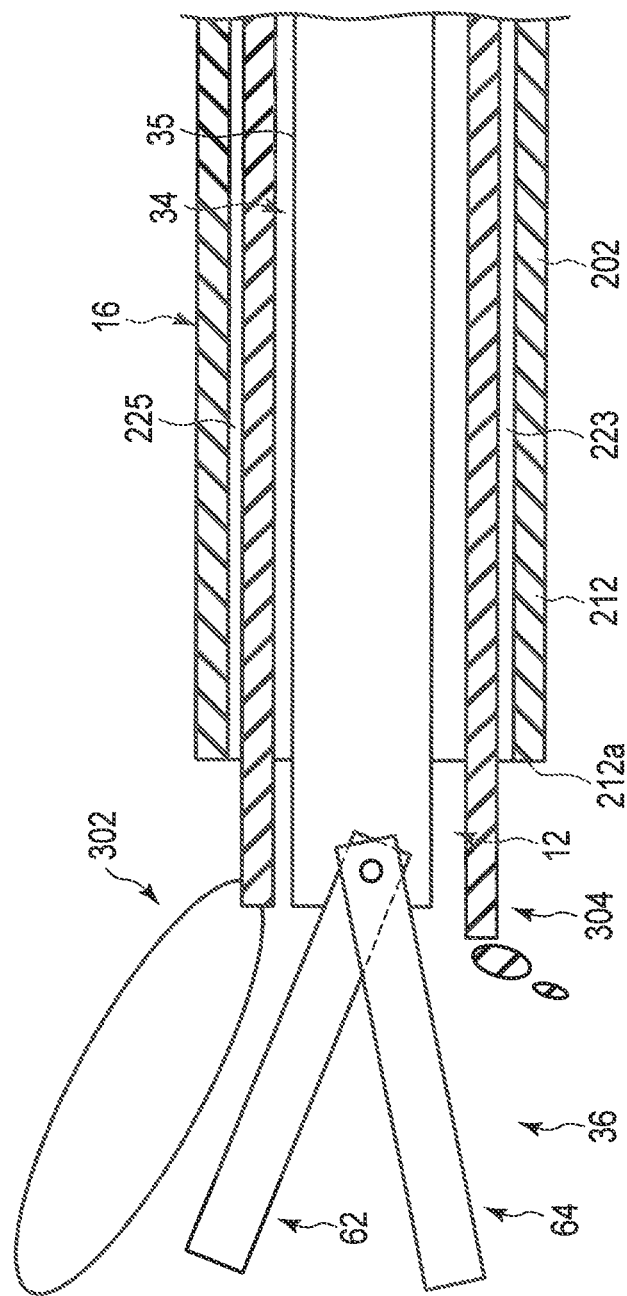
FIG. 10 is a schematic view showing a state in which a fluid supply unit is mounted on a treatment instrument according to a modified example of the first embodiment, and a state in which first and second grasping sections are relatively movable, and various treatment devices are inserted through a lumen between an outer circumferential surface of a shaft and an inner circumferential surface of a tube.

In this embodiment, the end effector 36 of a type in which the first grasping section 52 moves with respect to the second grasping section 64 has been explained as an example. That is, an example in which the first grasping section 62 is movable with respect to the fixed second grasping section 64 has been explained. As shown in FIG. 10, it is also preferable to use an end effector 36 of a type in which both of the first and second grasping sections 62 and 64 move. That is, it is also preferable that both the first grasping section 52 and the second grasping section 64 are of a structure that can be relatively close to and spaced apart from each other. In this case, the fluid supply instrument 92 may be attached to either one of the first and second grasping sections 62 and 54 and used. The fluid supply instrument 92 may also be attached to both of the first and second grasping sections 62 and 64.

It is also preferable to arrange an appropriate device in some parts of the lumens 223, 225, 227, and 229 on the outer circumference of the shaft 34. That is, as shown in FIG. 10, the plurality of lumens 223, 225, 227, and 229 can be used as insertion channels of various treatment devices. Through the lumen 223 among the plurality of lumens 223, 225, 227, and 229, a fluid supply catheter 304 is inserted. Through another lumen 225, a snare 302 is inserted. These treatment devices (fluid supply catheter 304 and snare 302) can be used together with the treatment instrument 12.

The fluid supply catheter 304 is arranged, for example, in the lumen 223, separately from the fluid channel 216a of the second conduit 216, the fluid channel 232 of the main body 212, and the fluid channel 214a of the first conduit 214. The fluid supply catheter 304 can apply, for example, a chemical liquid or the like to a desired position. The snare 302 is arranged, for example, in the lumen 225. For example, the snare 302 can bind and cut off an object to resected such as a polyp. The object to be resected can be suctioned and stored in the suction tank 20b using the same lumen 225 or other lumens 223, 227, and 229.

Furthermore, in the treatment instrument 12 according to the first embodiment, an example of using high-frequency energy has been explained. However, thermal energy generated by a heater may also be used together with the high-frequency energy or instead of the high-frequency energy. For example, in the case of using the thermal energy together with the high-frequency energy, the heater may be arranged between the electrode 72 and the movable member 74. For example, the heater may be arranged on the back surface of the electrode 72. In the case of, for example, using the thermal energy instead of the high frequency energy, the electrode 72 may be replaced with a heat transfer plate or the heater.

Furthermore, an example of the second grasping section 54 using the high-frequency energy in cooperation with the first electrode 72 has been explained. Alternatively, ultrasonic vibration may be transmitted to the rod 52 of the shaft 34. When high-frequency energy is used while the ultrasonic vibration is transmitted to the rod 52 in a state where the living tissue is grasped between the first and second grasping sections 62 and 64, the living tissue can be cut while being sealed.

Second Embodiment

A second embodiment will be explained with reference to FIG. 11A to FIG. 12C. The present embodiment is a modified example of the first embodiment which includes a modified example, in which, to omit detailed explanations, the same symbols as those in the first embodiment will be applied whenever possible to the same members or the members with the same functions as those explained in the first embodiment.

Figure 11A:
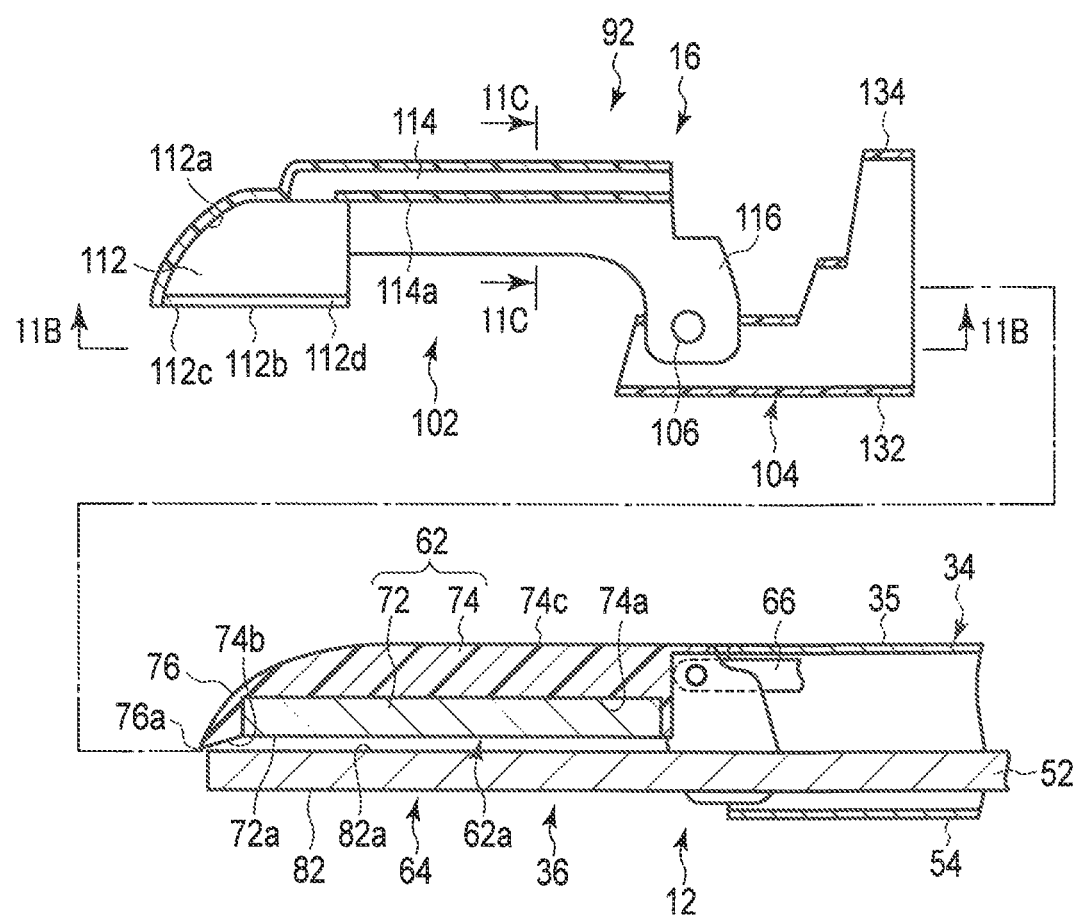
FIG. 11A is a schematic cross-sectional view showing a state in which a fluid supply instrument of a fluid suction/fluid supply unit is to be mounted on the first grasping section of the end effector of the treatment instrument of a treatment system according to the second embodiment.

As shown in FIG. 11A, in this embodiment, a port 114 of a main body 102 of a fluid supply instrument 92 is in a shape of a tubular pipe 114b, and not in a shape of a half-pipe. The outer circumferential surface of the pipe 114b comes into contact with or comes into closely contact with a back surface 74c of a movable member 74. The distal end of the port 114 communicates with a gap G. The pipe 114b may be formed of a flexible material having flexibility similar to that of a tube Main body 212, or may be formed of a hard material such as a hard plastic material or a metal material.

In the first embodiment, in order to fix the main body 102 of the fluid supply instrument 92 to the first grasping section 62 of the treatment instrument 12, an example in which the holding arm (holding portion) 118 is provided on the connection section 116 of the main body 102 of the fluid supply instrument 92 has been explained. Here, an example of a cover 112 that is provided with a fitting portion 112d to be fitted to an edge portion 74b of the movable member 74 of a first grasping section 62 will be explained. It is also preferable that both a holding arm 118 and the fitting portion 112d are formed on the main body 102 of the fluid supply instrument 92.

As shown in FIG. 12C, the fitting portion 112d protrudes inward from an edge portion of the cover 112. An inner circumferential surface 112d of the cover 112 is configured to support a position close to the edge portion 74b of a distal end portion 76 of the movable member 74. Furthermore, the fitting portion 112d can be configured to hold the edge portion 74b of the movable member 74. Therefore, the fitting portion 112d is configured to be fitted to the edge portion 74b of a grasping surface 62a. That is, the fitting portion 112d is configured to maintain a state in which the cover 112 and the port 114 rotate together with the first grasping section 62.

At this time, as shown in FIG. 12A and FIG. 12B, a gap G (fluid channel F) similar to that explained in the first embodiment is formed between the fluid supply instrument 92 and the first grasping section 62.

In this state, when a switch 48a is pressed, a fluid source 18 is operated, and a fluid (liquid) is supplied from the fluid source 18 to a fluid channel F between the port 114 of the fluid supply instrument 92 and the back surface 74c of the first grasping section 62, through a tube 22a, a first port 256 of a tube unit 94, a tubular main body 252 of a connection portion 204, a fluid channel 216a of a second conduit 216 of the tube unit 94, a fluid channel 232 of a convex portion 222 of the tube main body 212, and a fluid channel 214a of a first conduit 214. Therefore, the fluid is supplied to an outer circumference of a blood vessel from between the distal end of the Movable member 74 of the first grasping section 62 and the distal end of the fluid supply instrument 92. In this state, an energy source 14 is configured to apply a high-frequency current (high-frequency energy) between a first electrode 72 and a second electrode 82 to appropriately seal the blood vessel.

When the fluid such as physiological saline is supplied to the blood vessel, the physiological saline is made to mainly flow toward the distal end side of the grasping surface 62a, making it difficult for the physiological saline to flow toward the proximal end side. Therefore, the energy can be efficiently used to seal the blood vessel. By supplying the physiological saline to the grasping surface 62a, the blood vessel temporarily sealed and joined can be prevented from sticking to the first grasping section 62, and causing the seal of the blood vessel to be released, when opening the first grasping section 62 with respect to the second grasping section 64, etc.

Third Embodiment

A third embodiment will be explained with reference to FIG. 13. This embodiment is a modified example of the first and second embodiments, in which, to omit detailed explanations, the same symbols as those in the first and second embodiments will be applied whenever possible to the same members or the members with the same functions as those explained in the first and second embodiments.

In the first and second embodiments, an example in which the first electrode 72 is fixed to the movable member 74 has been explained. Here, as shown in FIG. 13, a movable member 74 rotates a grasping surface 62a wiper-like or seesaw-like in accordance with a living tissue. Specifically, a turning body (electrode holding member) 78 is rotatably supported on the movable member 74 by a pin 78a. The turning body 78 holds an electrode 72.

Here, a back surface 74c of the movable member 74 is formed in the same manner as explained in the second embodiment. Therefore, as explained in the second embodiment, the treatment can be performed appropriately while flowing the liquid. It is of course preferable to use the port 114 explained in the first embodiment.

Fourth Embodiment

A fourth embodiment will be explained with reference to FIG. 14A and FIG. 14B. This embodiment is a modified example of the first to third embodiments, in which, to omit detailed explanations, the same symbols as those in the first to third embodiments will be applied whenever possible to the same members or the members with the same functions as those explained in the first to third embodiments.

Here, a modified example of a tube 202 of a tube unit 94 will be explained.

Figure 14A:
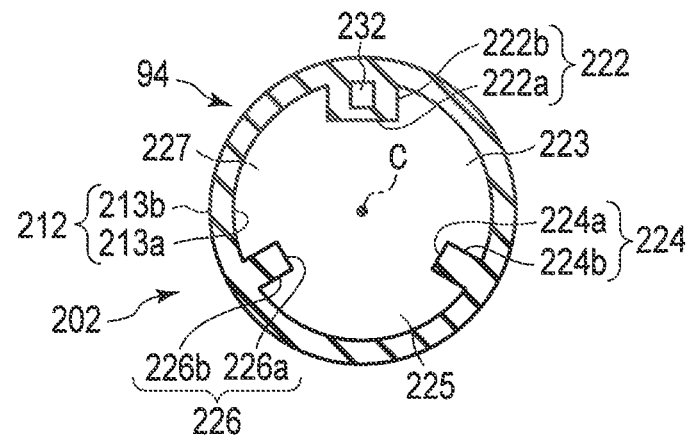
FIG. 14A is a schematic view showing a tube main body of a tube unit of a fluid suction/fluid supply unit of a treatment system according to the fourth embodiment viewed from a position taken along line 6A-6A in FIG. 1.
Figure 14B:
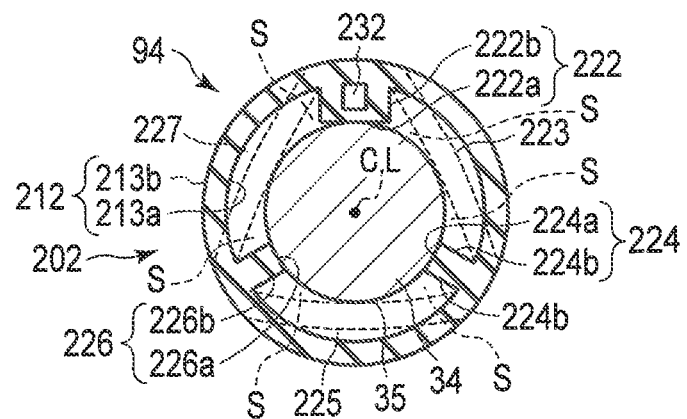
FIG. 14B is a schematic view showing a state in which the shaft is inserted through the tube main body of the tube unit shown in FIG. 14A.

As shown in FIG. 14A, convex portions 222, 224, and 226 are formed every 60° with respect to a central axis C. As shown in FIG. 14B, in a state where a shaft 34 is inserted through the tube 202, the convex portion 222 forms lumens 223 and 227. The convex portion 224 forms lumens 223 and 225. The convex portion 226 forms lumens 225 and 227. In this state, when a negative pressure is applied to the inside of the tube 202, an inner circumferential surface 213a of a tube main body 212 may come into contact with or be brought into close contact with an outer circumference of the shaft 34 as shown by a broken line in FIG. 14B. Even in this case, the convex portions 222, 224, and 226 maintain the distance (that is, an inward protruding length from the inner circumferential surface 213a) between the inner circumferential surface 213a of the tube main body 212 and convex surfaces 222a, 224a, and 226a in a state where the negative pressure is applied to the inner side of the tube main body 212. A space S is formed respectively at a position adjacent to the convex portion 222 in the circumferential direction, a position adjacent to the convex portion 224 in the circumferential direction, and a position adjacent to the convex portion 226 in the circumferential direction. Therefore, each of the spaces S are maintained as a suction channel.

Fifth Embodiment

A fifth embodiment will be explained with reference to FIG. 15A and FIG. 15B. This embodiment is a modified example of the first to fourth embodiments, in which, to omit detailed explanations, the same symbols as those in the first to fourth embodiments will be applied whenever possible to the same members or the members with the same functions as those explained in the first to fourth embodiments.

Here, a modified example of a tube 202 of a tube unit 94 will be explained.

Figure 15A:
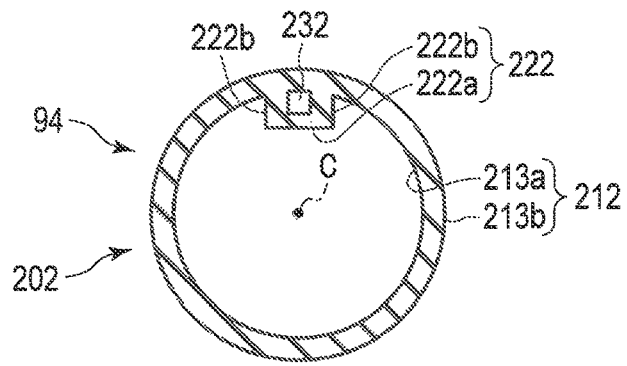
FIG. 15A is a schematic view showing a tube main body of a tube unit of a fluid suction/fluid supply unit of a treatment system according to the fifth embodiment viewed from a position taken along line 6A-6A in FIG. 1.

As shown in FIG. 15A, only one convex portion 222 is formed on an inner circumferential surface 213a of a main body 212 of the tube 202 of the tube unit 94. As shown in FIG. 15B, when a shaft 34 is inserted through the tube 202, an outer circumference of the shaft 34 comes in contact with a convex surface 222a of the convex portion 222, and a position of the inner circumferential surface 213a of the tube main body 212 that faces the convex surface 222a comes in contact with the outer circumference of the shaft 34. In this state, the convex portion 222 forms lumens 223 and 225. At this time, unlike what was explained in the first to fourth embodiments, a central axis C of the tube 202 and a longitudinal axis L of the shaft 34 do not coincide with each other, and are in a shifted position.

Figure 15B:
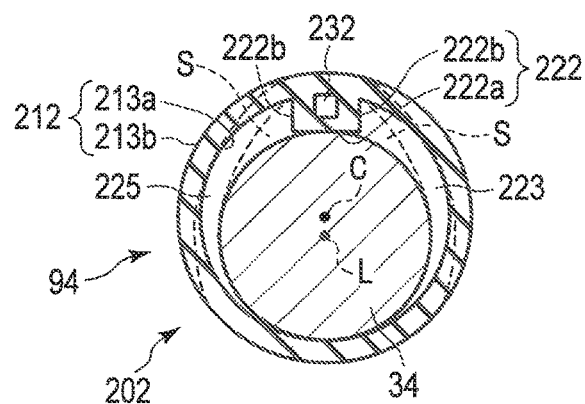
FIG. 15B is a schematic view showing a state in which the shaft is inserted through the tube main body of the tube unit shown in FIG. 15A.

In this state, when a negative pressure is applied to the inside of the tube 202, the inner circumferential surface 213a of the tube main body 212 is brought into close contact with the outer circumference of the shaft 34 as shown by a broken line in FIG. 15B. The convex portion 222 maintains a distance between the inner circumferential surface 213a of the tube main body 212 and the convex surface 222a in a state where the negative pressure is applied to the inner side of the tube main body 212. Even in this case, each of spaces S are formed at a position adjacent to the convex portion 222 in the circumferential direction. Therefore, each of the spaces S is maintained as a suction channel.

Sixth Embodiment

Figure 16:
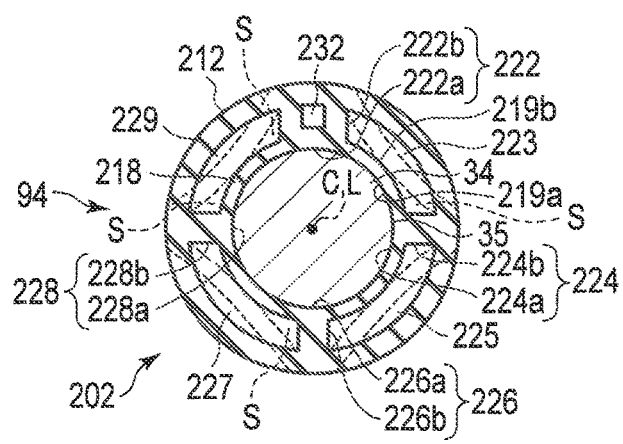
FIG. 16 is a schematic view showing a state in which the shaft inserted through a tube main body of a tube unit of a fluid suction/fluid supply unit of a treatment system according to the sixth embodiment is viewed from a posit on taken along line 6A-6A in FIG. 1.

In the following, the sixth embodiment will be explained with reference to FIG. 16. This embodiment is a modified example of the first to fifth embodiments, in which, to omit detailed explanations, the same symbols as those in the first to fifth embodiments will be applied whenever possible to the same members or the members with the same functions as those explained in the first to fifth embodiments.

Here, a modified example of a tube 202 of a tube unit 94 will be explained.

A main body 212 of the tube 202 have an inner tube 218 formed integrally with convex portions 222, 224, 226, and 228. Convex surfaces 222x, 224a, 226a, and 228a of the convex portions 222, 224, 226, and 228 are flush with an inner circumferential surface 219a of the inner tube 218.

Therefore, the convex surfaces 222a, 224a, 226a, and 228a and the inner circumferential surface 219a of the inner tube 218 cooperate with each other to form an inner circumferential curved surface. The inner tube 218 is located inside the tube main body 212 and is configured to cover an outer circumferential surface 35 of a shaft 34. The inner tube 218 forms a lumen 223 between the convex portions 222 and 224, a lumen 225 between the convex portions 224 and 226, a lumen 227 between the convex portions 226 and 228, and a lumen 229 between the convex portions 228 and 222.

The convex portions 222, 224, 226, and 228 maintain a distance between an inner circumferential surface 213a of the tube main body 212 and the convex surfaces 222a, 224a, 226a, and 228a and the outer circumferential surface 219b of the inner tube 218 in a state where a negative pressure is applied to the inner side of the tube main body 212. When the negative pressure is applied between the inner side of the tube main body 212 and the outer circumferential surface 219b of the inner tube 218, each pair of side surfaces 222b, 224b, 226b, 228b of the convex portions 222, 224, 226, and 228 and the inner circumferential surface 213a of the tube main body 212 form each space (gap) S between the pair of side surfaces 222b, 224b, 226b, and 228b and the outer circumferential surface 219b of the inner tube 218. Therefore, each of the spaces S is maintained as a suction channel.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A tube configured to be mounted and used on an outer side of a shaft of a treatment instrument, the tube comprising:
    a tube main body that extends along a longitudinal axis defined by a distal end and a proximal end, and that includes an inner circumferential surface;
    a first convex portion that is provided along the longitudinal axis, and that includes a first convex surface which is protruded inward in a radial direction of the tube main body with respect to the inner circumferential surface of the tube main body, and which is configured to come into contact with an outer circumferential surface of the shaft; and
    a pipe line that extends in the first convex portion along the longitudinal axis, and that is configured to pass a fluid,
    wherein:
    the first convex portion and the inner circumferential surface of the tube main body form a first lumen with the outer circumferential surface of the shaft, and
    the first lumen is located at a position adjacent to the first convex portion in a circumferential direction of the longitudinal axis.

2. The tube according to claim 1, wherein
    the first lumen is configured to suction an aspirated material from the distal end of the tube main body, and to discharge the aspirated material to a proximal side of the tube main body, and
    the pipe line is configured to pass the fluid flowing in from the proximal end of the tube main body and flowing out to a distal side of the tube main body.

3. The tube according to claim 2, wherein
    the first lumen is configured to communicate with a suction port at a proximal side of the first lumen, and
    the pipe line is configured to communicate with a fluid supply port at a proximal side of the pipe line.

4. The tube according to claim 1, wherein the tube main body includes a through-hole which is configured to penetrate the inner circumferential surface of the tube main body and an outer circumferential surface of the tube main body.

5. The tube according to claim 1, wherein the first convex portion maintains a distance between the inner circumferential surface of the tube main body and the first convex surface in a state where a negative pressure is applied to an inner side of the tube main body.

6. The tube according to claim 1, wherein the first convex portion includes a pair of side surfaces faced in opposite directions from each other along the longitudinal axis between the first convex surface and the inner circumferential surface of the tube main body, and forms a space between each of the pair of side surfaces and the outer circumferential surface of the shaft by the pair of side surfaces and the inner circumferential surface of the tube main body when a negative pressure is applied inside the tube main body.

7. The tube according to claim 1, comprising a second convex portion that is provided along the longitudinal axis at a position which is shifted in the circumferential direction with respect to the first convex portion, and that includes a second convex surface which is protruded inward in the radial direction of the tube main body with respect to the inner circumferential surface of the tube main body, and which is configured to come into contact with the outer circumferential surface of the shaft.

8. The tube according to claim 7, wherein the second convex portion maintains a distance between the inner circumferential surface of the tube main body and the second convex surface in a state where a negative pressure is applied to an inner side of the tube main body.

9. The tube according to claim 7, wherein the second convex portion and the inner circumferential surface of the tube main body form a plurality of second lumens, in cooperation with the first convex portion, and in cooperation with the outer circumferential surface of the shaft, and
    the plurality of second lumens are provided at positions adjacent to the second convex portion in the circumferential direction of the longitudinal axis.

10. The tube according to claim 1, comprising a first conduit that is formed integrally with the distal end of the tube main body, that protrudes on a distal side with respect to the distal end of the tube main body, and that is configured to communicate with the pipe line.

11. The tube according to claim 1, comprising a second conduit that is formed integrally with the proximal end of the tube main body, that protrudes on a proximal side with respect to the proximal end of the tube main body, and that is configured to communicate with the pipe line.

12. A tube unit comprising:
    the tube according to claim 1; and
    a connection portion that is provided on a proximal end of the tube, and that includes:
        a housing including:
            a first through-hole through which the tube main body is inserted, and
            a second through-hole through which the shaft is configured to be inserted;
        a first seal member which is provided on an edge portion of the first through-hole, and which seals between an outer circumferential surface of the tube main body and the housing;

a second seal member which is provided on an edge portion of the second through-hole, and which is configured to seal between the outer circumferential surface of the shaft and the housing; and a suction port which is provided on the housing and which communicates with the proximal end of the tube main body.

13. The tube unit according to claim 12, wherein the connection portion includes a fluid supply port that is provided on the housing and that communicates with the pipe line.

14. A suction/fluid supply unit comprising:

the tube according to claim 1;

a conduit that is formed integrally with the distal end of the tube main body, that protrudes on a distal side from the distal end of the tube main body, and that communicates with the pipe line; and a fluid supply instrument that is configured to be mounted on an end effector of the treatment instrument, and that includes a port which is connected to the conduit.

\* \* \* \* \*